United States Patent
Platscher et al.

(10) Patent No.: US 9,796,666 B2
(45) Date of Patent: Oct. 24, 2017

(54) AMINOACID LIPIDS

(71) Applicant: Merck Patent GmbH, Darmstadt (DE)

(72) Inventors: Michael Wilhelm Platscher, Schlatt (CH); Raymond Behrendt, Singen (DE); Viola Groehn, Dachsen (CH); Simone Rachel Hoertner, Zurich (CH); Marco Silvio Passafaro, Thayngen (CH); Finn Bauer, Bedford, MA (US)

(73) Assignee: MERCK PATENT GmbH, Darmstadt (DE)

( * ) Notice: Subject to any disclaimer, the term of this patent is extended or adjusted under 35 U.S.C. 154(b) by 90 days.

(21) Appl. No.: 14/385,178

(22) PCT Filed: Mar. 11, 2013

(86) PCT No.: PCT/EP2013/000699
§ 371 (c)(1),
(2) Date: Sep. 15, 2014

(87) PCT Pub. No.: WO2013/135360
PCT Pub. Date: Sep. 19, 2013

(65) Prior Publication Data
US 2015/0030670 A1    Jan. 29, 2015

(30) Foreign Application Priority Data
Mar. 16, 2012   (EP) .................................... 12001793

(51) Int. Cl.
C07C 237/30 (2006.01)
C07C 271/22 (2006.01)
C07C 237/08 (2006.01)
C07C 237/10 (2006.01)
A61K 9/127 (2006.01)
C07C 59/185 (2006.01)
C07C 237/06 (2006.01)
C07C 237/22 (2006.01)

(52) U.S. Cl.
CPC .......... *C07C 237/30* (2013.01); *A61K 9/1272* (2013.01); *C07C 59/185* (2013.01); *C07C 237/06* (2013.01); *C07C 237/08* (2013.01); *C07C 237/10* (2013.01); *C07C 237/22* (2013.01); *C07C 271/22* (2013.01); *C07C 2603/18* (2017.05); *Y02P 20/55* (2015.11)

(58) Field of Classification Search
CPC .................................................... C07C 237/30
See application file for complete search history.

(56) References Cited

U.S. PATENT DOCUMENTS

| 4,144,036 | A | 3/1979 | Cummings |
| 5,416,016 | A | 5/1995 | Low et al. |
| 5,498,633 | A | 3/1996 | Santaniello et al. |
| 6,030,954 | A | 2/2000 | Wu et al. |
| 6,214,388 | B1 | 4/2001 | Benz et al. |
| 6,306,993 | B1 | 10/2001 | Rothbard et al. |
| 6,316,024 | B1 | 11/2001 | Allen et al. |
| 6,335,434 | B1 | 1/2002 | Guzaev et al. |
| 6,495,663 | B1 | 12/2002 | Rothbard et al. |
| 6,861,514 | B2 | 3/2005 | Cook et al. |
| 6,965,049 | B2 | 11/2005 | Tsuchida et al. |
| 2002/0049163 | A1 | 4/2002 | Cook et al. |
| 2002/0131965 | A1 | 9/2002 | Rothbard et al. |
| 2003/0138490 | A1 | 7/2003 | Hu et al. |
| 2003/0162719 | A1 | 8/2003 | Rothbard et al. |
| 2004/0162261 | A1 | 8/2004 | Tsuchida et al. |
| 2005/0025969 | A1* | 2/2005 | Berning ........... A61K 47/48015 428/403 |
| 2005/0063979 | A1 | 3/2005 | Pickl et al. |
| 2006/0111274 | A1 | 5/2006 | Rothbard et al. |
| 2010/0028450 | A1 | 2/2010 | Vasu |
| 2012/0294924 | A1 | 11/2012 | Tice et al. |

FOREIGN PATENT DOCUMENTS

| EP | 1420010 A1 | 5/2004 |
| WO | 79/00515 A1 | 8/1979 |
| WO | 98/52614 A2 | 11/1998 |
| WO | 99/66063 A2 | 12/1999 |
| WO | 02/094185 A2 | 11/2002 |
| WO | 03/039594 A2 | 5/2003 |
| WO | 2007/087341 A2 | 8/2007 |
| WO | 2009/129387 A2 | 10/2009 |
| WO | 2012/148891 A1 | 11/2012 |

OTHER PUBLICATIONS

International Search Report dated Jun. 13, 2013 issued in corresponding PCT/EP2013/000699 application (pp. 1-3).

(Continued)

*Primary Examiner* — Benjamin Packard
(74) *Attorney, Agent, or Firm* — Millen White Zelano and Branigan, PC; John Sopp; Csaba Henter

(57) ABSTRACT

The present invention is directed to a new class of lipids, more specifically ether-lipids having a polar headgroup, as well as vesicles comprising these lipids, methods of their preparation as well as their uses in medical applications, wherein the ether-lipids are represented by general formula I

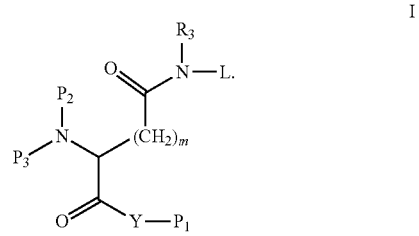

20 Claims, No Drawings

(56) References Cited

OTHER PUBLICATIONS

S. Zalipsky, "Functionalized Poly(ethylene glycol) for Preparation of Biologically Relevant Conjugates", Bioconjugate Chem., vol. 6, No. 2 (1995) pp. 150-165.

S.K.E. Messerschmidt et al., "Targeted Lipid-Coated Nanoparticles: Delivery of Tumor Necrosis Factor-Functionalized Particles to Tumor Cells", Journal of Controlled Release, vol. 137 (2009) pp. 69-77.

G. Kokotos et al., "Synthesis of 2-Oxo Amide Triacylglycerol Analogues and Study of Their Inhibition Effect on Pancreatic and Gastric Lipases", Chem. Eur. J., vol. 6, No. 22 (2000) pp. 4211-4217.

D.I. Magee et al., "Use of the Ramberg-Backlund Rearrangement for the Synthesis of Medium and Large Heterocyclic Alkenes: Stereoselective Olefin Formation", J. Org. Chem., vol. 65, No. 24 (2000) pp. 8367-8371.

J.H. Fendler et al., "Catalysis in Micellar and Macromolecular Systems", Academic Press 1975.

K. Shinoda, "The Formation of Micelles", Academic Press, N.Y. 1963, Chapter 1, pp. 1-96.

L.M. Canfield et al., "Incorporation of Beta-Carotene into Mixed Micelles", Methods in Enzymology, vol. 189 (1990) pp. 418-422.

M. El-Gorab et al., "Solubilization of Beta-Carotene and Retinol into Aqueous Solutions of Mixed Micelles", Biochem. Biophys. Acta., vol. 306 (1973) pp. 58-66.

R.C. Larock "Comprehensive Organic Transformations", VCH Publishers, Inc. NY (1989).

T.W. Greene et al., "The Role of Protective Groups in Organic Synthesis", Protective Groups in Organic Synthesis, Third Edition, Wiley, NY (1999) pp. 1-16.

J.H. Felgner et al., "Enhanced Gene Delivery and Mechanism Studies with a Novel Series of Cationic Lipid Formulations", The Journal of Biological Chemistry, vol. 269, No. 4 (Jan. 28, 1994) pp. 2550-2561.

I. Solodin et al., "A Novel Series of Amphiphilic Imidazolinium Compounds for in Vitro and in Vivo Gene Delivery", Biochemistry, vol. 34, No. 41 (1995) pp. 13537-13544.

G. Blume et al., "Specific Targeting with Poly(ethylene glycol)-Modified Liposomes: Coupling of Homing Devices to the Ends of the Polymeric Chains Combines Effective Target Binding with Long Circulation Times", Biochem. Biophys. Acta., vol. 1149 (1993) pp. 180-184.

T.M. Allen et al., "A New Strategy for Attachment of Antibodies to Sterically Stabilized Liposomes Resulting in Efficient Targeting to Cancer Cells", Biochem. Biophys. Acta., vol. 1237 (1995) pp. 99-108.

F.A. Carey et al., "Advanced Organic Chemistry", 3rd Edition, Plenum Press, NY 1990.

* cited by examiner

AMINOACID LIPIDS

FIELD OF THE INVENTION

The present invention is directed to a new class of lipids, more specifically ether-lipids having a polar headgroup, and vesicles comprising these lipids, methods of their preparation as well as their uses in medical applications.

BACKGROUND OF THE INVENTION

Molecular recognition, such as between receptor ligand, antigen-antibody, DNA-protein, sugar-lectin, RNA-ribosome, etc. is an important principle underlying many biological systems and is being applied to many artificially created biological systems for use in medical applications, such as in artificial (micro- or nano-) particulate systems including polymeric beads, vesicular lipids, microemulsions, and the like.

One important example of a molecular recognition based application is the use of targeted delivery of diagnostic or therapeutic compounds, such as antiviral, chemotherapeutic or imaging agents, to specific sites, which allows to overcome the limitations associated with nonspecific delivery (such as in vivo clearance time, potential toxicity, problems associated with membrane transport of an agent and the like) and thus greatly increases their effectiveness. Various recognition-based strategies have been used to improve the delivery of compounds into the intracellular environment (i.e. to specific cell compartments) of a target cell to exert its biological activity, in particular delivery through specific transporters involving the use of biological or artificial carriers, such as viral vectors, cationic polymers, such as polylysine, polyarginine and the like (see, e.g. WO 79/00515, WO 98/52614), lipid carriers, and various other conjugate systems.

One widely used approach involves the use of lipid vesicles as artificial carriers, e.g. liposomes, micelles, nanoparticles, which have been extensively developed and analyzed as drug delivery vehicles due to their ability to reduce systemic exposure of a biologically active agent, thereby overcoming problems associated with degradation, solubility, etc. and providing an increase in blood circulation times. Actively targeted delivery of a biologically active agent involves derivatizing the lipids of the lipid vesicle (either prior or after vesicle formation) with a targeting ligand that serves to direct (or target) the vesicle to specific cell types such as cancer cells or cells specific to particular tissues and organs, such as hepatocytes, after in vivo administration (see, for example, U.S. Pat. No. 6,316,024 and U.S. Pat. No. 6,214,388; Allen et al., Biochim. Biophys. Acta, 1237:99-108 (1995); Blume et al., Biochim. Biophys. Acta, 1149: 180-184 (1993)). This may be accomplished by utilizing receptors that are overexpressed in specific cell types, which include for example folic acid receptor (overexpressed in a variety of neoplastic tissues, including breast, ovarian, cervical, colorectal, renal, and nasoparyngeal tumors), epidermal growth factor receptor (EGFR) (overexpressed in anaplastic thyroid cancer and breast and lung tumors), metastin receptor (overexpressed in papillary thyroid cancer), ErbB family receptor tyrosine kinases (overexpressed in a significant subset of breast cancers), human epidermal growth factor receptor-2 (Her2/neu) (overexpressed in breast cancers), tyrosine kinase-18-receptor (c-Kit) (overexpressed in sarcomatoid renal carcinomas), HGF receptor c-Met (overexpressed in esophageal adenocarcinoma), CXCR4 and CCR7 (overexpressed in breast cancer), endothelin-A receptor (overexpressed in prostate cancer), peroxisome proliferator activated receptor delta (PPAR-delta) (overexpressed in most colorectal cancer tumors), PDGFR A (overexpressed in ovarian carcinomas), BAG-1 (overexpressed in various lung cancers), soluble type II TGF beta receptor (overexpressed in pancreatic cancer), asialoglycoprotein receptor (overexpressed on hepatocytes), $\Box_v\Box_3$ integrin receptor (overexpressed in growing tumor vascularture), etc.

Any agent which selectively binds to such a specific receptor cell or tissue to be treated or assayed may be attached to a lipid vesicle and act as a targeting or receptor ligand. Typically, such targeting ligands have been attached to a lipid or lipid vesicle surface through a long chain (e.g. polymeric) linker. For example folic acid based conjugates have been used to provide a targeted delivery approach of a therapeutic compound useful for the treatment and/or diagnosis of a disease, allowing a reduction in the required dose of therapeutic compounds (see e.g. WO 02/094185, U.S. Pat. No. 6,335,434, WO 99/66063, U.S. Pat. No. 5,416,016). Likewise, the use of galactose- and galactosamine-based conjugates to transport exogenous compounds across cell membranes can provide a targeted delivery approach to the treatment of liver disease such as HBV and HCV infection or hepatocellular carcinoma while allowing a reduction in the required dose of therapeutic compounds required for treatment (see e.g. U.S. Pat. No. 6,030,954).

Another important example of a molecular recognition based application is the use of antigen display systems which involve presentation of both "self" and "foreign" proteins (antigens) to the immune system to generate T cell activation, modulation or tolerance. The receptor ligand interactions in antigen-presenting systems that contribute to the desired immune response or absence thereof are complex and difficult to assess, being influenced by various parameters such as ligand densities, presence of coreceptors, receptor ligand affinities and surface conditions. Thus a widely used approach involved using naturally occurring human cells (or parts thereof) whose primary function is antigen processing and presentation. But, while live cell based systems may be optimal for mimicking cell-cell interaction to achieve the desired induction of tolerance or immune response, they are dependent on a regulated expression of the surface molecules including possibly expression of additional "costimulatory" and/or adhesion molecules on its surface membrane at a sufficient therapeutic level. Currently known artificial systems range from genetically engineered subcellular antigen presenting vesicles, which carry the molecules required for antigen presentation and T-lymphocyte activation or inhibition on their surface (WO 03/039594) to systems on the basis of cell-sized, biodegradable microspheres based, antigen presenting system (WO 07/087,341).

Clearly, there are still drawbacks to the above, molecular recognition based technologies and there remains a need in the art for a versatile and efficient artificial carrier system for use in molecular recognition based applications such as targeted delivery or antigen presentation, including simple and economic methods of their preparation.

The present application provides a new class of lipids and vesicles comprising these lipids for use as a carrier or display system, which allows overcoming the limitations described above.

SUMMARY OF THE INVENTION

The present invention is directed to a new class of lipids and vesicles comprising these lipids for use in various medical applications. More specifically the present invention is directed to ether-lipid compounds that are characterized by at least two ether-linked hydrocarbon chains and a headgroup comprising a short, straight-chain amino acid having up to 6 carbon atoms, in free, protected or activated form or optionally derivatized with at least one spacer group.

Specifically, in one embodiment, the present invention relates to a compound of general formula I

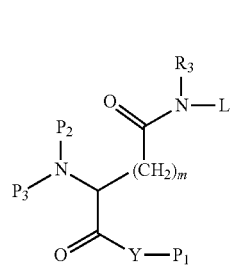

wherein
Y represents O, N, S or a covalent linkage
$P_1$ represents H, an Y-protecting group or an Y-activating group or a spacer group,
$P_2$, $P_3$ represent independently of each other H, an amino-protecting group or a spacer group, or $P_2$ and $P_3$ form together with the N to which they are bound a ring structure,
L is a group of formula (a)

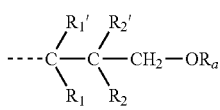

wherein the dashed line represents the linkage to N,
$R_1$, represent H or a group of formula —$(CH_2)_2$—$OR_{b1}$,
$R_{1'}$, represent H or a group of formula —$(CH_2)_2$—$OR_{b2}$,
$R_2$ represents H or a group of formula —$CH_2$—$OR_c$,
$R_{2'}$ represents H or a group of formula —$OR_d$ or —$CH_2$—$OR_d$,
$R_3$ represents H or a group of formula —$(CH_2)_2$—$OR_e$ or —$(CH_2)_3$—$OR_e$,
$R_a$, $R_{b1}$, $R_{b2}$, $R_c$, $R_d$, $R_e$ represent independently of each other a saturated or unsaturated, straight or branched hydrocarbon chain,
m is 1, 2 or 3,
with the proviso that at least one of $R_1$, $R_{1'}$, $R_2$, $R_{2'}$, $R_3$ is not H.

The compounds of the invention include all possible stereoisomers of the compounds, such as geometric isomers, e.g. Z and E isomers (cis and trans isomers), and optical isomers, e.g. diastereomers and enantiomers, in either pure form or in mixtures thereof.

In one embodiment, the invention is directed towards non-derivatized lipid compounds, wherein neither $P_1$, $P_2$, $P_3$ is a spacer group. More specifically, the non-derivatized lipid compounds include (i) lipid compounds in free form, wherein neither of $P_1$, $P_2$, $P_3$ is an activating or protecting group, (ii) protected lipid compounds, wherein at least one of $P_1$, $P_2$, $P_3$ is a protecting group, and (iii) activated lipid compounds, wherein $P_1$ is an activating group.

In another embodiment, the invention is directed towards lipid-spacer derivatives, wherein at least one of $P_1$, $P_2$, $P_3$ is a spacer group.

The compounds of the present invention comprise all possible permutations of groups $R_1$, $R_{1'}$, $R_2$, $R_{2'}$, $R_3$ and the substructures $R_a$, $R_{b1}$, $R_{b2}$, $R_c$, $R_d$, $R_e$ thereof.

In a first embodiment of a compound of formula I, group $R_3$ is H. More specifically, either (i) $R_3$ is H and both $R_1$ and $R_{1'}$ are H, or (ii) $R_3$ is H and both $R_2$ and $R_{2'}$ are H. Thus, the invention is directed towards compounds of formula Ia,

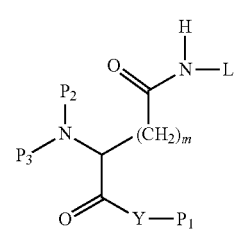

wherein L is a group of formula (a)

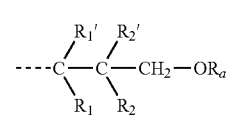

and wherein $P_1$, $P_2$, $P_3$, Y, $R_1$, $R_{1'}$, $R_2$, $R_{2'}$, $R_a$, and m are defined as above for a compound of formula I.

More specifically, the invention is directed towards compounds of formula Ia, wherein L is a group of formulas (b) or (c)

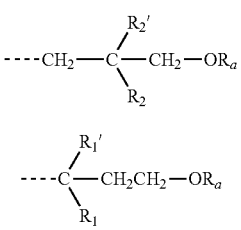

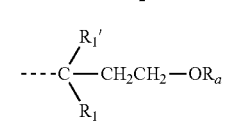

wherein $P_1$, $P_2$, $P_3$, Y, $R_1$, $R_{1'}$, $R_2$, $R_{2'}$, $R_a$, and m are defined as above, with the proviso that in formula (b) one of $R_2$ and $R_{2'}$ is not H, and in formula (c) one of $R_1$ and $R_{1'}$ is not H.

In a second embodiment, $R_1$, $R_{1'}$, $R_2$, $R_{2'}$, are H and $R_3$ is either a group of formula —$(CH_2)_2$—$OR_e$ or —$(CH_2)_3$—$OR_e$. Thus, the invention is directed towards compounds of formula Ib,

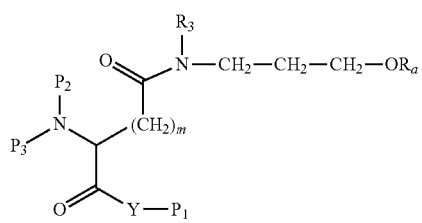

wherein $R_3$ is a group of formula —$(CH_2)_2$—$OR_e$ or —$(CH_2)_3$—$OR_e$, and $P_1$, $P_2$, $P_3$, Y, $R_a$, $R_e$ and m are defined as above for a group of formula I.

In another aspect the present invention is directed towards compositions in the form of vesicles (present compositions), e.g. liposomes, micelles, nanoparticles and the like. The vesicles of the invention comprise at least one compound of the invention or a mixture of various compounds of the invention, optionally in admixture with one or more other vesicle-forming compounds.

In another aspect the present invention is directed towards a method for preparing a compound and composition of the invention.

Another aspect of the present invention relates to a kit comprising a compound or a composition of the invention, preferably in lyophilized form.

The compounds and compositions of the present invention find use as a delivery vehicle e.g. for the targeted delivery of one or more bioactive agents or for use in an antigen display system. This aspect of the present compounds and compositions is part of an international application filed concurrently, which is incorporated herein in its entirety.

These and other aspects of the invention will become more apparent from the following specification and claims.

DETAILED DESCRIPTION OF THE INVENTION

As employed above and throughout the disclosure, certain terms, unless otherwise indicated, shall be understood to have the following meanings:

The term "compound" as used herein (alone or in combination with "present" or "of the invention" or "lipid") refers to a compound of the invention, which comprise a linear, bifunctional amino acid at the head group, more specifically a 2-amino-alkanedioic acid (having up to six carbon atoms), such as aspartic acid, glutamic acid, and the like. The compounds of the invention include both "non-derivatized (lipid) compounds", which are either in free form ("free (lipid) compound"), in protected form ("protected (lipid) compound") or in activated form ("activated (lipid) compound") and thus carry no covalently attached spacer groups, as well as "derivatized (lipid) compounds" (or "lipid spacer derivative"), which are conjugates of non-derivatized (lipid) compounds with one or more spacer groups.

A protected or activated (lipid) compound refers to a compound of the invention which has been modified site-specifically to contain a protecting or activating group, respectively. The modification takes place at the head group, more specifically at the reactive sites of the amino acid, more preferably at the N- and/or Y-groups with suitable protecting or activating groups (e.g. in form of $P_1$, $P_2$, $P_3$), respectively, known in the art.

A "lipid spacer derivative" refers to a compound of the invention which has been modified site-specifically to contain a spacer group. The modification takes place at the head group, more specifically at the reactive sites of the amino acid, more preferably at the N- and/or Y-group (or CO-group if Y is a covalent bond) with suitable spacer groups (e.g. in form of $P_1$, $P_2$, $P_3$) known in the art using known coupling techniques.

The term "composition" or "present composition" refers to a composition which comprises at least one compound of the invention. Exemplary compositions include vesicles or vesicular compositions, which in their broadest interpretation include any association of at least one lipid compound of the invention with other materials and structures. Thus, suitable vesicular compositions include, but are not limited to, liposomes, micelles, microspheres, nanoparticles and the like. In one particular embodiment a vesicular composition refers to a spherical entity having an internal void or a solid core. Vesicles may be formulated from synthetic or naturally-occurring lipids, including one or more compounds of the present invention, and mixtures thereof. In any given vesicle, the lipids may be in the form of a monolayer or a bilayer. In the case of more than one mono- or bilayer, the mono- or bilayers are generally concentric. The lipid vesicles include such entities commonly referred to as liposomes (i.e. a vesicle including one or more concentrically ordered lipid bilayer(s) with an internal void), micelles (i.e. a vesicle including a single lipid monolayer with an internal void), nanospheres, and the like. Thus, the lipids may be used to form a unilamellar vesicle (comprised of one monolayer or bilayer), an oligolamellar vesicle (comprised of about two or about three monolayers or bilayers) or a multilamellar vesicle (comprised of more than about three monolayers or bilayers). Alternatively they may be used to coat a preexisting vesicle such as a nanoparticle, e.g. a nanosphere. An internal void of the vesicles may be filled with a liquid, including, for example, an aqueous liquid, a gas, a gaseous precursor, and/or a solid material, including, for example, one or more biologically active agents. In another particular embodiment, a vesicular composition refers to compositions in form of clusters, tubes and the like.

The compositions of the invention may comprise one or more biologically active agents, which are either embedded or enclosed therein or attached thereto (covalently and non-covalently). More specifically, the vesicular compositions of the invention may comprise in the internal void one or more biologically active agents (for delivery functions) and/or may be derivatized at their surface with one or more biologically active agents (for either targeting or display functions). This is part of an application filed concurrently, which is incorporated herein in its entirety.

The term "co-lipid" or "vesicle-forming (co-)lipid" as used herein refers to lipids which may optionally be present as additional lipids in the lipid compositions of the invention and may include acyclic and cyclic, saturated or unsaturated lipids of natural or synthetic origin. As used herein a co-lipid may be a neutral lipid, a cationic lipid or an anionic lipid. A cationic lipid has a positive net charge and may include lipids such as N-[1-(2,3-dioleoyloxy)propyl]-N,N,N-trimethyl ammonium salts, e.g. the methylsulfate (DOTAP), DDAB, dimethyldioctadecyl ammonium bromide; 1,2-diacyloxy-3-trimethylammonium propanes, (including but not limited to: dioleoyl, dimyristoyl, dilauroyl, dipalmitoyl and distearoyl; also two different acyl chain can be linked to the glycerol backbone); N-[1-(2,3-dioloyloxy)propyl]-N,N-dimethyl amine (DODAP); 1,2-diacyloxy-3-dimethylammonium propanes, (including but not limited to: dioleoyl, dimyristoyl, dilauroyl, dipalmitoyl and distearoyl; also two different acyl chain can be linked to the glycerol backbone); N-[1-(2,3-dioleyloxy)propyl]-N,N,N-trimethylammonium chloride (DOTMA); 1,2-dialkyloxy-3-dimethylammonium propanes, (including but not limited to: dioleyl, dimyristyl, dilauryl, dipalmityl and distearyl; also two different alkyl chain can be linked to the glycerol backbone); dioctadecylamidoglycylspermine (DOGS); 3β-[N—(N',N'-dimethylamino-ethane)carbamoyl]cholesterol (DC-Chol); 2,3-dioleoyloxy-N-(2-(sperminecarboxamido)-ethyl)-N,N-dimethyl-1-propanam-inium trifluoro-acetate (DOSPA); β-alanyl cholesterol; cetyl trimethyl ammonium bromide (CTAB); diC14-amidine; N-tert-butyl-N'-tetradecyl-3-tetradecylamino-propionamidine; 14Dea2; N-(alpha-trimethylammonioacetyl)didodecyl-D-glutamate chloride (TMAG); O,O'-ditetradecanoyl-N-(trimethylammonio-acetyl)diethanolamine chloride; 1,3-dioleoyloxy-2-(6-carboxy-spermyl)-propylamide (DOSPER); N,N,N',N'-tetramethyl-N,N'-bis(2-hydroxyethyl)-2,3-dioleoyloxy-1,4-butan-ediammonium iodide; 1-[2-(acyloxy)ethyl]2-alkyl(alkenyl)-3-(2-hydroxyethyl)-imidazolinium chloride derivatives (as described by Solodin et al. (1995) Biochem. 43:13537-13544), such as 1-[2-(9(Z)-octadecenoyloxy)ethyl]-2-(8(Z)-heptadecenyl-3-(2-hydroxyethyl) imidazolinium chloride (DOTIM), 1-[2-(hexadecanoyloxy)ethyl]-2-pentadecyl-3-(2-hydroxyethyl) imidazolinium chloride (DPTIM), 2,3-dialkyloxypropyl quaternary ammonium compound derivatives, containing a hydroxyalkyl moiety on the quaternary amine (see e.g. by Feigner et al. J. Biol. Chem. 1994, 269, 2550-2561), such as: 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-dimethyl-hydroxypropyl ammonium bromide (DORIE-HP), 1,2-dioleyloxypropyl-3-dimethyl-hydroxybutyl ammonium bromide (DORIE-HB), 1,2-dioleyloxypropyl-3-dimethyl-hydroxypentyl ammonium bromide (DORIE-Hpe), 1,2-dimyristyloxypropyl-3-dimethyl-hydroxylethyl ammonium bromide (DMRIE), 1,2-dipalmityloxypropyl-3-dimethyl-hydroxyethyl ammonium bromide (DPRIE), 1,2-disteryloxypropyl-3-dimethyl-hydroxyethyl ammonium bromide (DSRIE); cationic esters of acyl carnitines (as reported by Santaniello et al. U.S. Pat. No. 5,498,633); cationic triesters of phospahtidylcholine, i.e. 1,2-diacyl-sn-glycerol-3-ethyl-phosphocholines, where the hydrocarbon chains can be saturated or unsaturated and branched or non-branched with a chain length from $C_{12}$ to $C_{24}$, the two acyl chains being not necessarily identical. Neutral or anionic lipids have a neutral or anionic net charge, respectively. These can be selected from sterols or lipids such as cholesterol, phospholipids, lysolipids, lysophospholipids, sphingolipids or pegylated lipids with a neutral or negative net change. Useful neutral and anionic lipids thereby include: phosphatidylserine, phosphatidylglycerol, phosphatidylinositol (not limited to a specific sugar), fatty acids, sterols, containing a carboxylic acid group for example, cholesterol, cholesterol sulfate and cholesterol hemisuccinate, 1,2-diacyl-sn-glycero-3-phosphoethanolamine, including, but not limited to, DOPE, 1,2-diacyl-glycero-3-phosphocholines and sphingomyelin. The fatty acids linked to the glycerol backbone are not limited to a specific length or number of double bonds. Phospholipids may also have two different fatty acids.

The present invention is directed to a new class of lipids and vesicles comprising these lipids for use in various medical applications. More specifically the present invention is directed to ether-lipid compounds H-L, wherein L is a lipidic group comprising at least two ether-linked hydrocarbon chains and H is a headgroup comprising a short, straight-chain amino acid (□-amino acid) having up to 6 carbon atoms and derivatives thereof.

More specifically, the present invention relates to a compound of general formula I

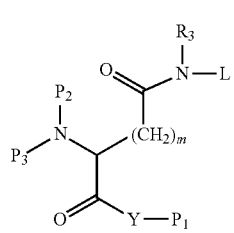

wherein
Y represents O, N, S or a covalent linkage,
$P_1$ represents H, an Y-protecting group or an Y-activating group or a spacer group, $P_2$, $P_3$ represent independently of each other H, an amino-protecting group or a spacer group, or $P_2$ and $P_3$ form together with the N to which they are bound a ring structure,
L is a group of formula (a)

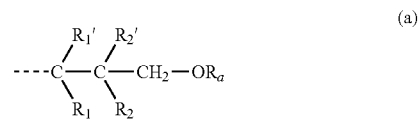

wherein the dashed line represents the linkage to N,
$R_1$, represent H or a group of formula $—(CH_2)_2—OR_{b1}$,
$R_{1'}$, represent H or a group of formula $—(CH_2)_2—OR_{b2}$,
$R_2$ represents H or a group of formula $—CH_2—OR_c$,
$R_{2'}$ represents H or a group of formula $—OR_d$ or $—CH_2—OR_d$,
$R_3$ represents H or a group of formula $—(CH_2)_2—OR_e$ or $—(CH_2)_3—OR_e$,
$R_a$, $R_{b1}$, $R_{b2}$, $R_c$, $R_d$, $R_e$ represent independently of each other a saturated or unsaturated, straight or branched hydrocarbon chain,
m is 1, 2 or 3,
with the proviso that at least one of $R_1$, $R_{1'}$, $R_2$, $R_{2'}$, $R_3$ is not H.

In a first embodiment of a compound of formula I, group $R_3$ is H. More specifically, either (i) $R_3$ is H and $R_1$ and $R_{1'}$ are H, or (ii) $R_3$ is H and $R_2$ and $R_{2'}$ are H.

Thus, in this first embodiment the invention is directed towards compounds of formula Ia,

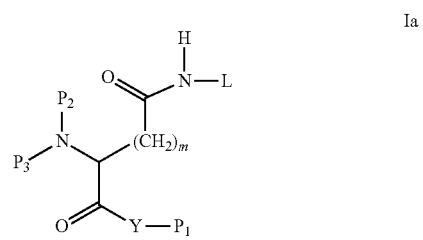

wherein L is a group of formula (a)

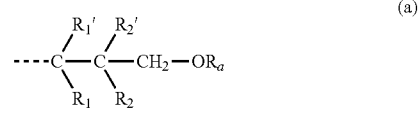

and wherein $P_1$, $P_2$, $P_3$, Y, $R_1$, $R_{1'}$, $R_2$, $R_{2'}$, $R_a$, and m are defined as above for a compound of formula I.

More specifically, the invention is directed towards compounds of formula Ia, wherein L is a group of formulas (b) or (c)

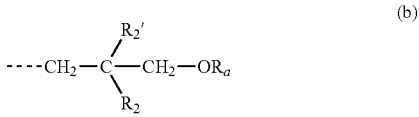

-continued

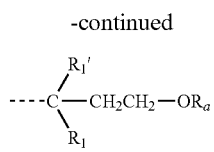
(c)

wherein $P_1$, $P_2$, $P_3$, Y, $R_1$, $R_{1'}$, $R_2$, $R_{2'}$, $R_a$ are defined as above, with the proviso that in formula (b) one of $R_2$ and $R_{2'}$ is not H, and in formula (c) one of $R_1$ and $R_{1'}$ is not H.

In one preferred embodiment of group (b) $R_2$ is H and $R_{2'}$ is —$OR_d$ or —$CH_2$—$OR_d$. In another preferred embodiment of group (b) $R_2$ is —$CH_2$—$OR_c$ and $R_{2'}$ is —$OR_d$ or $R_{2'}$ is —$CH_2$—$OR_d$.

Thus, the invention is preferably directed to compounds of formula Ia, wherein L is a group of formula (b1), (b2), (b3) or (b4):

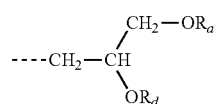
(b1)

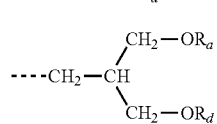
(b2)

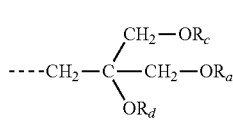
(b3)

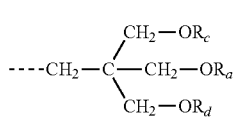
(b4)

wherein the dashed line represents the linkage to N, and wherein $R_a$, $R_c$ and $R_d$ are independently of each other a saturated or unsaturated, straight or branched hydrocarbon chain.

In one preferred embodiment of group (c), one of $R_1$ and $R_{1'}$ is H. In another preferred embodiment of group (c) neither of $R_1$ and $R_{1'}$ is H.

Thus, the invention is preferably also directed to compounds wherein L is a group of formula (c1) or (c2):

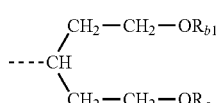
(c1)

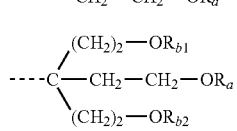
(c2)

wherein $R_a$, $R_{b1}$, $R_{b2}$ are defined as above.

In a second embodiment of a compound of formula I, groups $R_1$, $R_{1'}$, $R_2$, $R_{2'}$ are H and $R_3$ is either a group of formula —$(CH_2)_2$—$OR_e$ or —$(CH_2)_3$—$OR_e$.

Thus, in this second embodiment the invention is directed towards compounds of formula Ib,

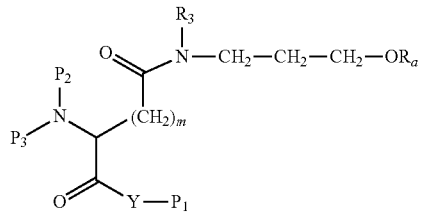
Ib wherein $R_3$ is a group of formula —$(CH_2)_2$—$OR_e$ or —$(CH_2)_3$—$OR_e$, and $P_1$, $P_2$, $P_3$, Y, $R_a$, $R_e$ and m are defined as above for a group of formula I.

Preferred embodiments of the invention are thus compounds of formula I (or formula Ia) represented by compounds of formulas II or III

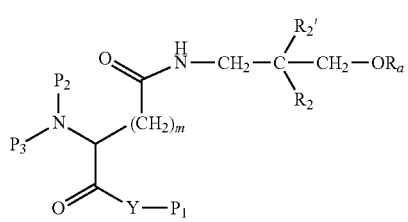
II

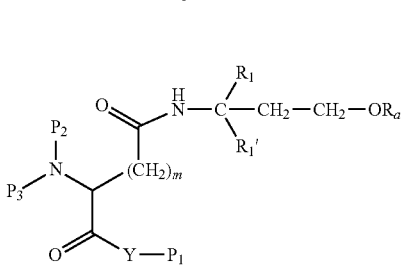
III wherein

Y represents O, N, S or a covalent linkage, $P_1$ represents H, an Y-protecting group or an Y-activating group or a spacer group, $P_2$, $P_3$ represent independently of each other H, an amino-protecting group or a spacer group, or $P_2$ and $P_3$ form together with the N to which they are bound a ring structure, $R_1$ represents H or a group of formula —$(CH_2)_2$—$OR_{b1}$, $R_{1'}$ represent H or a group of formula —$(CH_2)_2$—$OR_{b2}$, $R_2$ represents H or a group of formula —$CH_2$—$OR_c$, $R_{2'}$ represents H or a group of formula —$OR_d$ or —$CH_2$—$OR_d$, $R_a$, $R_{b1}$, $R_{b2}$, $R_c$, $R_d$ represent independently of each other a saturated or unsaturated, straight or branched hydrocarbon chain, m is 1, 2 or 3, with the proviso that in formula II one of $R_2$ and $R_{2'}$ is not H, and in formula III one of $R_1$ and $R_{1'}$ is not H.

More specific embodiments of compounds of formula II are compounds of formula IIa, IIb, IIc or IId,

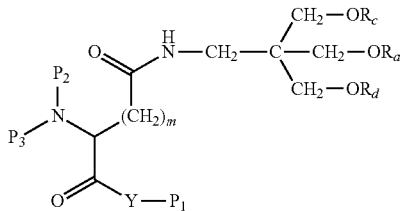

IIa

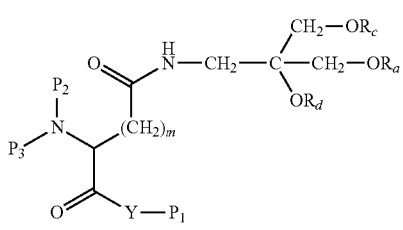

IIb

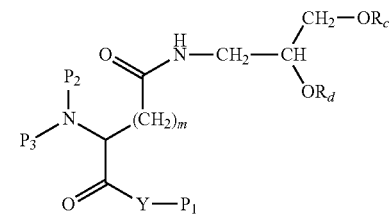

IIc

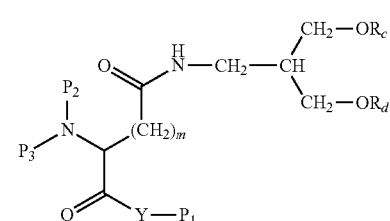

IId wherein
Y represents O, N, S or a covalent linkage,
$P_1$ represents H, an Y-protecting group or an Y-activating group or a spacer group,
$P_2$, $P_3$ represent independently of each other H, an amino-protecting group or a spacer group, or $P_2$ and $P_3$ form together with the N to which they are bound a ring structure,
$R_a$, $R_c$, $R_d$ represent independently of each other a saturated or unsaturated, straight or branched hydrocarbon chain,
m is 1, 2 or 3.

More specific embodiments of compounds of formula III are compounds of formula IIIa or IIIb,

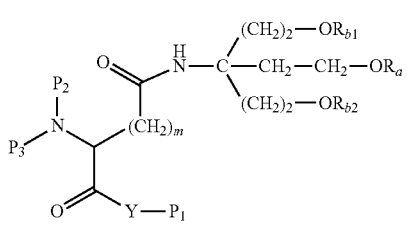

IIIa

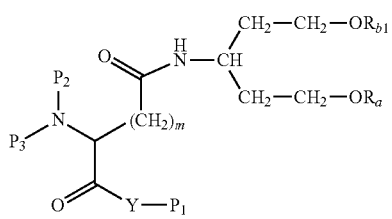

IIIb wherein
Y represents O, N, S or a covalent linkage,
$P_1$ represents H, a Y-protecting group or a Y-activating group or a spacer group,
$P_2$, $P_3$ represent independently of each other H, an amino-protecting group or a spacer group, or $P_2$ and $P_3$ form together with the N to which they are bound a ring structure,
$R_a$, $R_{b1}$, $R_{b2}$ represent independently of each other a saturated or unsaturated, straight or branched hydrocarbon chain,
m is 1, 2 or 3.

Other preferred embodiments of compounds of formula I (or formula Ib) are represented by compounds of formulas IVa and IVb,

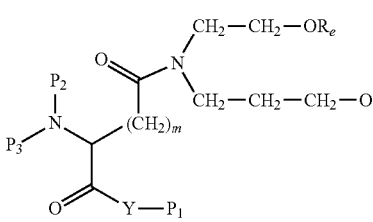

IVa

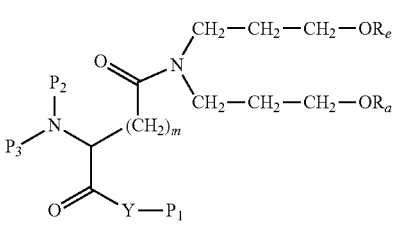

IVb wherein
Y represents O, N, S or a covalent linkage,
$P_1$ represents H, an Y-protecting group or an Y-activating group or a spacer group,
$P_2$, $P_3$ represent independently of each other H, an amino-protecting group or a spacer group, or $P_2$ and $P_3$ form together with the N to which they are bound a ring structure,
$R_a$, $R_e$ represent independently of each other a saturated or unsaturated, straight or branched hydrocarbon chain, and
m is 1, 2 or 3.

A person skilled in the art will appreciate that the compounds of the present invention contain one or more chiral centers and/or double bonds and therefore, may exist as stereoisomers, such as double-bond isomers (i.e., geometric isomers, e.g. Z/E isomers or cis/trans isomers), enantiomers or diastereomers. Accordingly, when stereochemistry at chiral centers is not specified, the chemical structures depicted herein encompass all possible configurations at those chiral centers including the stereoisomerically pure form (e.g., geometrically pure, enantiomerically pure or diastereomerically pure) the enriched form (e.g., geometrically enriched, enantiomerically enriched or diastereomerically enriched) and enantiomeric and stereoisomeric mixtures. The individual isomers may be obtained using the corresponding isomeric forms of the starting material. Alternatively, enantiomeric and stereoisomeric mixtures can be resolved into their component enantiomers or stereoisomers using separation techniques or chiral synthesis techniques well known to the skilled artisan. The compounds of the invention described herein may also exist in several tautomeric forms including the enol form, the keto form and mixtures thereof. Accordingly, the structures depicted herein encompass all possible tautomeric forms of the illustrated compounds.

The term "saturated or unsaturated, straight or branched hydrocarbon chain" as used herein refers to a saturated or unsaturated, straight or branched hydrocarbon chain having 6 to 30, preferably 10 to 22 carbon atoms.

The term "saturated" in combination with hydrocarbon chain refers to a straight or branched alkyl chain, containing 6 to 30, preferably 10 to 22 carbon atoms. Examples include, but are not limited to, capryl (decyl), undecyl, lauryl (dodedecyl), myristyl (tetradecyl), cetyl (hexadecyl), stearyl (octadecyl), nonadecyl, arachidyl (eicosyl), heneicosyl, behenyl (docosyl), tricosyl, tetracosyl, pentacosyl, including branched isomers thereof, e.g. isolauryl, anteisolauryl, isomyristyl, anteisomyristyl, isopalmityl, anteisopalmityl, isostearyl, anteisostearyl or phytanyl (3,7,11,15-tetramethylhexadecanyl).

The term "unsaturated" in combination with hydrocarbon chain indicates that fewer than the maximum possible number of hydrogen atoms are bonded to each carbon in the chain giving rise to one or more carbon-carbon double or triple bonds. In preferred embodiments, the number of unsaturated bond(s) in an unsaturated hydrocarbon chain is 1, 2, 3 or 4, preferably 1 or 2.

Examples of alkenyl groups include, but are not limited to, monounsaturated alkenyls, such as decenyl, undecenyl, dodecenyl, palmitoleyl, heptadecenyl, octadecenyl (elaidyl, oleyl, ricinolenyl), nonadecenyl, eicosenyl, heneicosenyl, docosenyl (erucyl), tricosenyl, tetracosenyl, pentacosenyl, and the branched chain isomers thereof, as well as polyunsaturated alkenyls such as octadec-9,12-dienyl (linoleyl, elaidolinoleyl), octadec-9,12,15-trienyl (linolenyl, elaidolinolenyl), 9(Z), 11(E), 13(E)-octadecatrienyl (eleostearyl), and eicos-5,8,II,14-tetraenyl.

Examples of alkynyl groups include, but are not limited to hexadec-7-ynyl and octadec-9-ynyl.

The term "branched" in combination with hydrocarbon refers to a hydrocarbon chain having a linear series of carbon atoms as a main chain with at least one substituent of one or more carbon atoms as subordinate chain (or branching groups). Examples of subordinate chains include one or more (C1-6)alkyl groups, such as methyl, ethyl, propyl, isopropyl, n-butyl, sec-butyl group, tert-butyl, pentyl, hexyl and the like, one or more (C1-6)alkenyl groups, such as vinyl, allyl, propenyl, isopropenyl, 2-butenyl and the like, or one or more (C1-6)alkynyl groups, such as ethynyl, propynyl, butynyl and the like. Preferred subordinate chains are (C1-6)alkyl groups, most preferred methyl and ethyl.

The compounds of the invention comprise preferably at least two hydrocarbon chains, preferably 2, 3, 4, 5 or 6 hydrocarbon chains, most preferably 2 or 3 hydrocarbon chains, wherein the main chain of the hydrocarbon chains are the same or different, preferably the same, and are selected from an alkyl chain, an alkenyl chain, and an alkynyl chain, preferably an alkyl and an alkenyl chain. In one preferred embodiment, the compounds of the invention carry two alkyl chains, which can be the same or different, preferably the same.

In a specific embodiment of a compound of the invention the hydrocarbon chains $R_a$, $R_{b1}$, $R_{b2}$, $R_c$, $R_d$, $R_e$ are preferably selected from myristyl, palmityl, stearyl, oleyl, linoleyl and phytanoyl.

The terms "alkyl", "alkoxy", "alkenyl", "alkynyl" as used herein with reference to groups $P_1$, $P_2$, $P_3$, have the following meanings:

The term "alkyl" refers to a straight or branched alkyl-chain, containing 1 to 12, preferably 1 to 8 carbon atoms. Examples of alkyl groups include, but are not limited to, methyl, ethyl, n-propyl, i-propyl, n-butyl, i-butyl, and t-butyl. The term "alkoxy" refers to an —O-alkyl radical. Examples of alkoxy groups include, but are not limited to, methoxy, ethoxy, and butoxy. The term "alkenyl" refers to a straight or branched unsaturated alkyl group having one or more carbon-carbon double bonds. The above alkyl, alkenyl, and alkoxy groups may be optionally substituted with further groups. Examples of substituents include, but are not limited to, halo, hydroxyl, amino, cyano, nitro, mercapto, alkoxycarbonyl, amido, carboxy, alkylsulfonyl, alkylcarbonyl, carbamido, carbamyl, carboxyl, thioureido, thiocyanato, sulfonamido, aryl, heteroaryl, cyclyl, and heterocyclyl.

The term "aryl" refers to an aromatic carbocyclic radical containing about 6 to about 10, preferably 5 to 7 carbon atoms. The aryl group may be optionally substituted with one or more aryl group substituents which may be the same or different, where "aryl group substituent" includes alkyl, alkenyl, alkynyl, aryl, aralkyl, hydroxy, alkoxy, aryloxy, aralkoxy, carboxy, aroyl, halo, nitro, trihalomethyl, cyano, alkoxycarbonyl, aryloxycarbonyl, aralkoxycarbonyl, acyloxy, acylamino, aroylamino, carbamoyl, alkylcarbamoyl, dialkylcarbamoyl, arylthio, alkylthio, alkylene and —NRR', wherein R and R' are each independently hydrogen, alkyl, aryl and aralkyl. Exemplary aryl groups include substituted or unsubstituted phenyl, naphthyl, pyrenyl, anthryl, and phenanthryl.

The term "heteroaryl" refers to an aryl moiety as defined above having at least one heteroatom (e.g., N, O, or S). Examples of a heteroaryl moiety include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

The term "(hetero)aryloxy" refers to an (hetero)aryl-O-group wherein the (hetero)aryl group is as previously described. Exemplary aryloxy groups include phenoxy and naphthoxy. The term "(hetero)aralkyl" refers to an (hetero)aryl-alkyl-group wherein (hetero)aryl and alkyl are as previously described. Exemplary aralkyl groups include benzyl, phenylethyl and naphthylmethyl. The term "(hetero)aralkyloxy" refers to an (hetero)aralkyl-O-group wherein the (hetero)aralkyl group is as previously described. An exemplary aralkyloxy group is benzyloxy.

The term "cycloalkyl" refers to a saturated or unsaturated, non-aromatic, cyclic hydrocarbon moiety having 6 to 10 carbon atoms, such as cyclohexyl or cyclohexen-3-yl. The term "heterocycloalkyl" refers to a cycloalkyl as defined herein having at least one ring heteroatom (e.g., N, O, or S), such as 4-tetrahydropyranyl or 4-pyranyl.

Aryl, heteroaryl, cycloalkyl, heterocycloalkyl as mentioned herein include both substituted and unsubstituted moieties, unless specified otherwise. Possible substituents on cycloalkyl, heterocycloalkyl, aryl, and heteroaryl include (C1-C10)alkyl, (C2-C10)alkenyl, (C2-C10)alkynyl, (C3-C8)cycloalkyl, (C5-C8)cycloalkenyl, (C1-C10)alkoxy, aryl, aryloxy, heteroaryl, heteroaryloxy, amino, $(C_1-C_{10})$alkylamino, (C1-C20)dialkylamino, arylamino, diarylamino, hydroxyl, halogen, thio, (C1-C10)alkylthio, arylthio, (C1-C10)alkylsulfonyl, arylsulfonyl, acylamino, aminoacyl, amidino, guanidine, ureido, cyano, nitro, acyl, acyloxy, carboxyl, and carboxylic ester. Cycloalkyl, heterocycloalkyl, aryl, and heteroaryl can also be fused with each other.

Group Y is O, N, S or a covalent linkage, preferably O or N, most preferably N. It is understood that if group Y is a covalent linkage, —$S_1$—$X_1$ is directly linked to the CO-group.

A "protecting group" is a moiety that can be selectively attached to and removed from a particular chemically reactive functional group in a molecule to prevent it from participating in undesired chemical reactions. The protecting group will vary depending upon the type of chemically reactive group being protected as well as the reaction conditions to be employed and the presence of additional reactive or protecting groups in the molecule. It is understood that the term "protecting group" if used in relation to a N-group (such as $P_1$ with Y being N, $P_2$ or $P_3$) in one of the compounds is an amino-protecting group, if used in relation to a COO-group (such as $P_1$ with Y being O) in one of the compounds is a carboxyl-protecting group, if used in relation to a CO-group (such as $P_1$ with Y being a covalent linkage) in one of the compounds is a carbonyl-protecting group, and if used in relation to a S-group (such as $P_1$ with Y being S) in one of the compounds is a sulfur-protecting group.

Representative protecting groups for various functional groups, such as e.g. carboxylic acid groups, amino groups, hydroxyl groups, thiol groups, carbonyl groups and the like, are well-known to those skilled in the art and are described, for example, in T. W. Greene and G. M. Wuts, Protecting Groups in Organic Synthesis, Third Edition, Wiley, N.Y., 1999, and references cited therein.

For the compounds of the present invention, a "carboxyl-protecting group" (e.g. group $P_1$ with Y being O) includes but is not limited to benzhydryl, benzyl esters, such as benzyl, and o- or p-nitrobenzyl, p-methoxybenzyl, alkyl esters, such as methyl, t-butyl, 4-pyridylmethyl 2-naphthylmethyl, 2,2-trichloroethyl, silyl esters, such as 2-trimethylsilyl, t-butyldimethylsilyl, t-butyldiphenylsilyl, 2-(trimethylsilyl)ethyl; orthoesters, such as trimethyl- or triethyl orthoacetate; oxazoline, allyl, 2-chloroallyl, phenacyl, acetonyl, p-methoxyphenyl. Preferred groups include benzyl, t-butyl.

An amide protecting group (e.g. group $P_1$ with Y being N) includes but is not limited to a phthalimide or a trifluoroacetamide protecting group.

An "amino-protecting group" includes both acyclic as well as cyclic protecting groups ($P_2$ and $P_3$), for example each of groups $P_2$ and $P_3$ may represent a protecting group which can be the same or different or $P_2$ and $P_3$ form together with the N to which they are bound a cyclic protecting group. Typical groups include, but are not limited to, carbamates, such as Boc (t-butyloxycarbonyl, Cbz (carboxybenzyl), Fmoc (fluorenylmethyloxycarbonyl), alloc (allyloxycarbonyl), methyl and ethyl carbamates; trityl, benzyl, benzylidene, tosyl and the like; cyclic imide derivatives, such as succinimide and phthalimide; amides, such as formyl, (un)substituted acetyl, and benzoyl; and trialkyl silyl groups, such as t-butyldimethylsilyl and triisopropylsilyl. Preferred amino-protecting groups include Boc, Cbz, Fmoc, benzyl, acetyl, benzoyl, trityl and the like.

The terms "activated" or "activating," for example, as used in connection with any of the terms "group", "amine group" "carboxyl group", "spacer group", refer to a chemical moiety that render a chemical functionality more sensitive to modification under certain reaction conditions such that the activated chemical functionality can react under appropriate conditions with a second chemical group thereby forming a covalent bond.

For example, an activating group may convert a poor leaving group into a good leaving group or increase (or decrease) susceptibility to nucleophilic attack or other chemical transformations.

Accordingly, a "carboxyl activating group" is meant to refer to a moiety that replaces the hydrogen or hydroxyl of a carboxyl group, thereby altering the chemical and electronic properties of the carboxyl group such that the carboxyl group is more susceptible to nucleophilic attack or substitution.

In embodiments in which the hydrogen of the carboxyl group is replaced, exemplary carboxyl activating groups include, for example, alkyl, aryl, aralkyl, heteroaryl, heterocyclyl, alkylcarbonyl, arylcarbonyl, aralkylcarbonyl, heteroarylcarbonyl, heterocyclylcarbonyl, C(S)O-aryl, C(S)O-alkyl, silyl or substituted alkylcarbonyl. An example of an aryl carboxyl activating group is pentahalophenyl, such as pentafluorophenyl, and an example of an alkylcarbonyl carboxyl activating group is acetyl or trifluoroacetyl. The carboxyl activating groups may be optionally substituted. An example of a substituted carboxyl activating group is substituted alkylcarbonyl, for example, carboxyl substituted alkylcarbonyl, such as succinyl (3-carboxylpropionyl).

Carboxyl activation in which the hydrogen of the —C(=O)—OH group is replaced may also involve the use of coupling agents, which are moieties that promote nucleophilic addition reactions, i.e. substituents which have a net electron withdrawing effect on the carbonyl. Such groups act to assist or promote the coupling of, or to improve the rate of the coupling of, carboxylate groups with compounds having reactive functionalities, for example, nucleophiles, including amino groups such as in the formation of amido functionality. Coupling agents are well known to one ordinarily skilled in the art and are described, for example, in Larock, R. C., Comprehensive Organic Transformations, VCH Publishers, Inc., NY (1989), and Carey, F. A., and Sundberg, R. J., Advanced Organic Chemistry, $3^{rd}$ Edition, Plenum Press, NY (1990), the disclosures of each of which are hereby incorporated herein by reference in their entireties.

Carboxyl activation in which the hydroxyl group of the —C(=O)—OH group is replaced includes e.g. replacing the hydroxyl by a moiety such as a halo group, such as fluoro, chloro, bromo or iodo, giving a carboxylic acid halide, which is more susceptible to nucleophilic attack or substitution.

Thus, typical activating or coupling groups include, but are not limited to, esters and amides such as hydroxybenzotriazole, imidazole, a nitrophenol, pentachlorophenol, N-hydroxysuccinimide, dicyclohexylcarbodiimide, N-hydroxy-N-methoxyamine, and the like; acid anhydrides such as acetic, formic, sulfonic, methanesulfonic, ethanesulfonic, benzenesulfonic, or p-tolylsulfonic acid anhydride, and the like; and acid halides such as the acid chloride, bromide, or iodide.

The activated carbonyl compound is obtained by reacting a reactive moiety of choice with the carbonyl compound using standard procedures. The activated carbonyl compound may be generated in situ, or may be provided in isolated form, as appropriate. Exemplary reactive moieties to obtain the activated compounds cited above include the respective groups containing isothiocyanate, isocyanate, monochlorotriazine, dichlorotriazine, mono- or di-halogen substituted pyridine, mono- or di-halo substituted diazine, maleimide, aziridine, sulfonyl halide, acid halide, hydroxysuccinimide ester, hydroxysulfosuccinimide ester, imido ester, hydrazine, azidonitrophenyl, azide, 3-(2-pyridyl dithio)proprionamide, glyoxal and aldehyde.

The term "spacer" or "spacer group" in conjunction with groups $P_1$, $P_2$, $P_3$ is used herein to refer to a bivalent branched or unbranched chemical group which allows to link the compound of the invention to a further moiety, i.e. a bioactive group in sufficient distance to eliminate any undesired interaction between compound and further moiety and/or to reduce any steric hindrance (caused by the compound itself or any other neighbouring molecules) that may impact the biological activity of the further moiety (such as affinity binding of ligands to their receptor). Depending on the intended use of a conjugate of ether-lipid and bioactive ligand, the spacer groups may be of different length and may be (hydrolytically, enzymatically and chemically) stable or may include a cleavable linkage. Cleavable linkages of the invention may be selected to be cleaved via any form of cleavable chemistry, e.g. chemical, enzymatic, hydrolytic and the like. Exemplary cleavable linkers include, but are not limited to, protease cleavable peptide linkers, nuclease sensitive nucleic acid linkers, lipase sensitive lipid linkers, glycosidase sensitive carbohydrate linkers, pH sensitive linkers, hypoxia sensitive linkers, photo-cleavable linkers, heat-labile linkers, enzyme cleavable linkers, ultrasound-sensitive linkers, x-ray cleavable linkers, etc.

Groups $P_1$, $P_2$, $P_3$ may represent independently of each other H, a protecting group or a spacer group. More specifically $P_1$ represents H, a Y-protecting group or a Y-activating group or a spacer group $S_1$; $P_2$ represents H, an amino-protecting group or a spacer group $S_2$; and $P_3$ represents H, an amino-protecting group or a spacer group $S_3$; or $P_2$ and $P_3$ form together with the N to which they are bound a ring structure.

It is understood that the spacers may or may not be end-group activated to allow for linkage of the spacer modified compound of the invention to a further moiety, such as bioactive group.

In specific embodiments, a "spacer group" (also termed groups $S_1$, $S_2$, $S_3$) represents a short spacer group or a long-chain spacer group selected from an alkylene chain optionally comprising one or more of the groups selected from ketone, ester, ether, amino, amide, amidine, imide, carbamate or thiocarbamate functions, glycerol, urea, thiourea, double bonds or aromatic rings.

More specifically, a short spacer group (or groups $S_1$, $S_2$, $S_3$) may be chosen from (C1-C12)alkyl, (C2-C12)alkenyl, aryl, aralkyl, heteroaryl.

A long-chain spacer group (or groups $S_1$, $S_2$, $S_3$) may be chosen from polymeric radicals of formula —W—(CH$_2$—)$_k$—W'—, wherein k is an integer between 13 and 3000, and W and W' are reactive groups able to react with amino, carboxyl, hydroxy or thio groups and wherein one or more of the non-adjacent CH$_2$ groups may independently be replaced by aryl, heteroaryl, —CH═CH—, —C≡C—, or a hydrophilic (or polar) group selected from —O—, —CO—, —CO—O—, —O—CO—, —NR'—, —NR'—CO—, —CO—NR'—, —NR'—CO—O—, —O—CO—NR'—, —NR'—CO—NR'—, and —O—CO—O—, wherein R' represents hydrogen or (C1-C12)alkyl. It is understood that replacing more than one non-adjacent CH$_2$ group by the same group may yield in polymeric chain having a specific repeating unit (e.g. a polyester, polyether, polyimide, etc).

Preferred spacer groups include hydrophilic polymeric radicals (with an increased affinity for aqueous solutions), i.e. polymers containing repeating structural units that comprise one or more of the above hydrophilic (or polar) groups in their alkylene backbone. Typical examples of hydrophilic polymeric radicals include polyoxy($C_2$-$C_3$)alkylenes (e.g. polyethylene glycol (PEG) or polypropylene glycol (PPG)), polysaccharides (e.g. dextran, pullulan, chitosan, hyaluronic acid), polyamides (e.g. polyamino acids, semisynthetic peptides and polynucleotides); polysialic acid, polyesters (e.g. polylactide (PLA), polylactid-co-glycolid (PLGA)), polycarbonates, polyethyleneimines (PEI), polyimides, polyvinyl acetate (PVA).

A preferred spacer is "PEG" or "polyethylene glycol", which encompasses any water-soluble poly(ethylene oxide). Typically, "PEG" means a polymer that contains a majority, e.g. >50%, of subunits that are —CH$_2$CH$_2$O—. Different forms of PEG may differ in molecular weights, structures or geometries (e.g., branched, linear, forked PEGs, multifunctional, and the like). PEGs for use in the present invention may preferably comprise one of the two following structures: "—O(CH$_2$CH$_2$O)$_m$—" or "—CH$_2$CH$_2$(CH$_2$CH$_2$O)$_m$—CH$_2$CH$_2$—," where m is 3 to 3000, and the terminal groups and architecture of the overall PEG may vary. As indicated above, depending on its use, PEG may be in end-capped form. When PEG is defined as "—O(CH$_2$CH$_2$O)$_m$—" the end capping group is generally a carbon-containing group typically comprised of 1-20 carbons and is preferably alkyl (e.g., methyl, ethyl or benzyl) although saturated and unsaturated forms thereof, as well as aryl, heteroaryl, cyclyl, heterocyclyl, and substituted forms of any of the foregoing are also envisioned. When PEG is defined as "—CH$_2$CH$_2$O(CH$_2$CH$_2$O)$_m$—CH$_2$CH$_2$—", the end capping group is generally a carbon-containing group typically comprised of 1-20 carbon atoms and an oxygen atom that is covalently bonded to the group and is available for covalently bonding to one terminus of the PEG. In this case, the group is typically alkoxy (e.g., methoxy, ethoxy or benzyloxy) and with respect to the carbon-containing group can optionally be saturated and unsaturated, as well as aryl, heteroaryl, cyclyl, heterocyclyl, and substituted forms of any of the foregoing. The other ("non-end-capped") terminus is typically a hydroxyl, amine or an activated group that can be subjected to further chemical modification when PEG is defined as "—CH$_2$CH$_2$CH$_2$(CH$_2$CH$_2$O)$_m$—CH$_2$CH$_2$—" In addition, the end-capping group can also be a silane.

A review for the preparation of various end-group functionalized or activated PEG is known in the art (see for example Zalipsky S., Bioconjug. Chem., 6, 150-165 (1995)).

In preferred embodiments the invention is directed to compounds of the following formulas V, VI and VII:

V

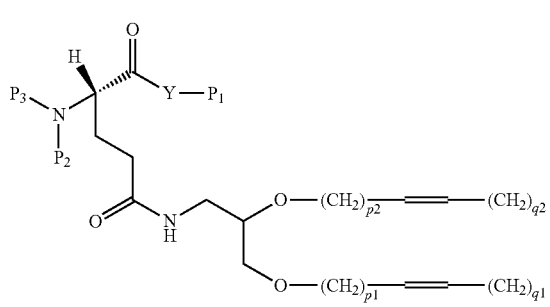

-continued

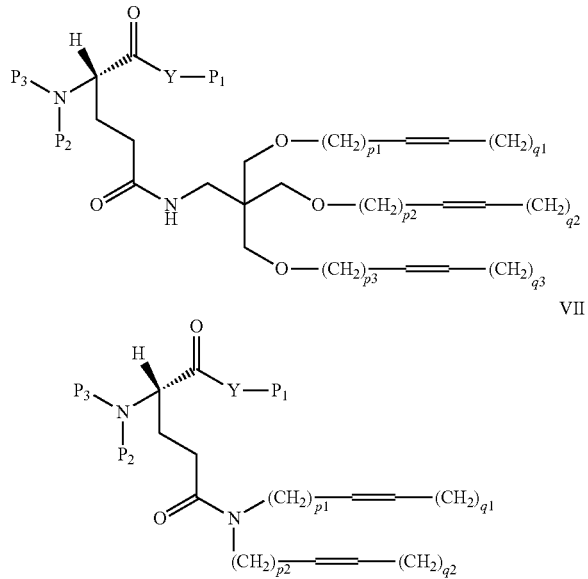

wherein
Y represents O, N, S or a covalent linkage,
$P_1$ represents H, an Y-protecting group or an Y-activating group or a spacer group,
$P_2$, $P_3$ represent independently of each other H, an amino-protecting group or a spacer group, or $P_2$ and $P_3$ form together with the N to which they are bound a ring structure,
p1, q1, p2, q2, p3, q3 are independently of each other 1 to 23, with the proviso that the sum of p1 and q1, p2 and q2, p3 and q3 is from 12 to 24.

In further aspects the present invention is directed towards a method for preparing a compound of the invention.

The compounds of the invention are particularly suitable for use in the preparation of vesicular compositions, such as liposomes, micelles and (lipid coated) nanoparticles.

Thus, in another aspect the present invention is directed towards vesicular compositions which are composed of at least one compound of the invention. Such vesicles comprise non-derivatized compounds or derivatized compounds comprising a spacer group or mixtures thereof. Optionally the vesicular compositions may comprise one or more other vesicle-forming lipids.

In one embodiment a vesicle may comprise lipid-spacer derivatives of the invention and other vesicle-forming lipids (co-lipids), preferably in a ratio from 1:200 to 200:1.

As those skilled in the art will recognize, once placed in possession of the present invention, vesicular compositions in form of lipid coated nanoparticles, liposomes, micelles, or other vesicles, may be readily prepared from the compounds of the invention using standard conditions known in the art.

Depending on the desired physical properties, vesicular compositions may be prepared from compounds of the invention optionally in combination with one or more co-lipids including stabilizing lipids. The particular stabilizing compounds which are ultimately combined with the present compounds may be selected as desired to optimize the properties of the resulting composition (and are readily identifiable by one skilled in the art without undue experimentation).

Vesicular compositions of the invention are particularly effective as carriers for the delivery of bioactive agents or as antigen presenting carriers.

The term "bioactive agent" as used herein refers to any synthetic or naturally occurring compound (in free form, salt form or solvated or hydrated form) having a biological activity, such as a targeting agent, an antigenic agent, a therapeutic agent or a diagnostic agent, preferably a therapeutic agent or a diagnostic agent.

The term "antigen-presenting system" (also termed "antigen display system") as used herein refers to a naturally occurring or synthetic system, which (i) can present at least one antigen (or part thereof) in such a way that the at least one antigen (or part thereof) can be recognized or bound by an immune effector molecule, e.g. a T-cell antigen receptor on the surface of a T cell, or (ii) is capable of presenting at least one antigen (or part thereof) in the form of an antigen-MHC complex recognizable by specific effector cells of the immune system, and thereby inducing an effective cellular immune response against the antigen (or part thereof) being presented.

Micellar vesicular compositions according to the invention may be prepared using any one of a variety of conventional micellar preparatory methods which will be apparent to those skilled in the art. These methods typically involve suspension of the lipid compound in an organic solvent, evaporation of the solvent, resuspension in an aqueous medium, sonication and centrifugation. The foregoing methods, as well as others, are discussed, for example, in Canfield et al., Methods in Enzymology, Vol. 189, pp. 418-422 (1990); El-Gorab et al, Biochem. Biophys. Acta, Vol. 306, pp. 58-66 (1973); Colloidal Surfactant, Shinoda, et al, Academic Press, N.Y. (1963) (especially "The Formation of Micelles", Shinoda, Chapter 1, pp. 1-88); Catalysis in Micellar and Macromolecular Systems, Fendler and Fendler, Academic Press, N.Y. (1975). The disclosures of each of the foregoing publications are incorporated by reference herein, in their entirety.

Optional stabilizing materials be combined with the compounds of the invention to stabilize the micellar compositions produced therefrom include lauryltrimethylammonium bromide, cetyltrimethylammonium bromide, myristyltrimethylammonium bromide, (C12-C16)alkyldimethylbenzylammonium chloride, cetylpyridinium bromide and chloride, lauryl sulphate, and the like. Other materials for stabilizing the micellar compositions, in addition to those exemplified above, would be apparent to one skilled in the art based on the present disclosure.

Liposomal vesicular compositions may comprise one or more non-derivatized compounds and/or one or more derivatized compounds (carrying a spacer group) optionally in combination with one or more further co-lipids and/or one or more stabilizing compounds. The present compound(s) (optionally in combination with the colipids) may be in form of a monolayer or bilayer. In the case of more than one mono- or bilayer, the mono- or bilayers are generally concentric. Thus, the present compounds (and optionally colipids) may be used to form a unilamellar liposome (comprised of one monolayer or bilayer), an oligolamellar liposome (comprised of two or three monolayers or bilayers) or a multilamellar liposome (comprised of more than three monolayers or bilayers).

(Co-)Lipids, which may be used in combination with the present compounds and in the formation of liposomal vesicular, compositions of the invention include preferably cationic lipids, phosphatidylcholine (PC), phosphatidyl-DL-glycerol (PG), L-α-phosphtidylethanolamine (PE), cholesterol, cholesteryl hemisuccinate tri salt (CHEMS), 1,2-dioleoyl-3-trimethylammonium-propane (DOTAP)

Other materials for use in the preparation of liposomal vesicular compositions of the invention, in addition to those exemplified above, would be apparent to one skilled in the art based on the present disclosure.

The amount of stabilizing material, such as, for example, additional amphipathic compound, which is combined with the present compounds may vary depending upon a variety of factors, including the specific structure of the present compound(s) of the invention selected, the specific stabilizing material(s) selected, the particular use for which it is being employed, the mode of delivery, and the like. The amount of stabilizing material to be combined with the present compounds and the ratio of stabilizing material to present compound, will vary and is readily determinable by one skilled in the art based on the present disclosure. Typically ratios higher than about 4:1, 3:1 or 2:1, of present compound to stabilizing lipid, are preferred.

The selection of suitable co-lipids and stabilizing compounds in the preparation of liposomal vesicular compositions of the invention would be apparent to a person skilled in the art and can be achieved without undue experimentation, based on the present disclosure.

A wide variety of methods are available in connection with the preparation of liposomal vesicular compositions of the invention. Accordingly, the liposomes may be prepared using any one of a variety of conventional liposome preparatory techniques which will be apparent to those skilled in the art. These techniques include ethanol injection, thin film technique, homogenizing, solvent dialysis, forced hydration, reverse phase evaporation, microemulsification and simple freeze-thawing, Using e.g. conventional microemulsification equipment. Additional methods for the preparation of liposomal vesicular compositions of the invention from the compounds of the present invention include, for example, sonication, chelate dialysis, homogenization, solvent infusion, spontaneous formation, solvent vaporization, controlled detergent dialysis, and others, each involving the preparation of liposomes in various ways. Typically, methods which involve ethanol injection, thin film technique, homogenizing and extrusion are preferred in connection with the preparation of liposomal compositions of the invention from the compounds of the present invention.

The size of the liposomes can be adjusted, if desired, by a variety of techniques, including extrusion, filtration, sonication and homogenization. Other methods for adjusting the size of the liposomes and for modulating the resultant liposomal biodistribution and clearance of the liposomes would be apparent to one skilled in the art based on the present disclosure. Preferably, the size of the liposomes is adjusted by extrusion under pressure through pores of a defined size. The liposomal compositions of the invention may be of any size, preferably less than about 200 nanometer (nm) in outside diameter.

Nanoparticulate vesicular compositions or nanoparticles are typically small particles having typically a diameter of less than 1 micron, preferably in the range of about 25-1000 nm, more preferably in the range of about 50-300 nm, most preferably in the range of about 60-200 nm. A nanoparticle can have any shape and any morphology. Examples of nanoparticles include nanopowders, nanoclusters, nanocrystals, nanospheres, nanofibers, and other geometries. A nanopolymer refers to a polymer that upon polymerization assembles to form a nanoparticle, such as, e.g., a nanorod, nanofiber, or nanosphere. A nanosphere refers to a type of nanoparticle that is approximately spherical in shape and may have a hollow core or a solid core.

In one embodiment, nanoparticles have a matrix core structure which may be formed using all types of materials and structures, including inorganic materials, such as metals, and organic materials, such as polymers including physiologically acceptable polymers. Non-limiting examples of such polymers include, for example, polyesters (such as poly(lactic acid), poly(L-lysine), poly(glycolic acid) and poly(lactic-co-glycolic acid)), poly(lactic acid-co-lysine), poly(lactic acid-graft-lysine), polyanhydrides (such as poly (fatty acid dimer), poly(fumaric acid), poly(sebacic acid), poly(carboxyphenoxy propane), poly(carboxyphenoxy hexane), copolymers of these monomers and the like), poly(anhydride-co-imides), poly(amides), poly(orthoesters), poly(iminocarbonates), poly(urethanes), poly(organophasphazenes), poly(phosphates), poly(ethylene vinyl acetate) and other acyl substituted cellulose acetates and derivatives thereof, poly(caprolactone), poly(carbonates), poly(amino acids), poly(acrylates), polyacetals, poly(cyanoacrylates), poly(styrenes), poly(vinyl chloride), polyvinyl fluoride), polyvinyl imidazole), chlorosulfonated polyolefins, polyethylene oxide, copolymers, polystyrene, and blends or co-polymers thereof. The nanoparticles may also include hydroxypropyl cellulose (HPC), N-isopropylacrylamide (NIPA), polyethylene glycol, polyvinyl alcohol (PVA), polyethylenimine, chitosan, chitin, dextran sulfate, heparin, chondroitin sulfate, gelatin, etc. as well as their derivatives, co-polymers, and mixtures thereof. A non-limiting method for making nanoparticles is described e.g. in U.S. Publication 2003/0138490. In another embodiment the core material may be selected from metals, alloys, metalloids, metal compounds such as metal oxides, inorganic compounds, and carbon-based materials, in particular carbon nanotubes, one-dimensional nanoparticles of fullerene $C_6o$, and three-dimensional nanoparticles of fullerene $C_{70}$.

Suitable examples of metals include, but are not limited to, noble or a platinum metal such as Ag, Au, Pd, Pt, Rh, Ir, Ru, and Os, transition metals such as Ti, Cr, Mn, Fe, Co, Ni, Cu, Zn, Zr, Nb, Mo, Ta, W, Re, and main group metals such as Al, Ga, In, Si, Ge, Sn, Sb, Bi, Te. It will be appreciated that some main group metals, in particular Si and Ge, are also commonly referred to as metalloids. Suitable examples of alloys include, but are not limited to, alloys of noble or platinum metal and transition metals, in particular alloys of silver and transition metals such as Ag/Ni, Ag/Cu, Ag/Co, and platinum and transition metals such as Pt/Cu, or noble or platinum alloys such as Ru/Pt. Non-limiting examples of inorganic compounds include, but are not limited to, $SiO_2$, metal compounds, in particular metal oxides such as $TiO_2$ and iron oxides.

A skilled person will know that the choice of material depends on the intended use of the nanoparticle.

Nanoparticles optionally include a functional group such as, for example, a carboxyl, sulhydryl, hydroxyl, or amino group, for covalently linking other compounds, such as linkers, to the surface of a nanoparticle. In other embodiments compounds, such as linkers, may be associated to a nanoparticle through other intermolecular forces such as Van-der-Waals forces, ionic interactions, hydrophobic interactions.

In certain embodiments, the nanoparticles can be associated with a bioactive agent (e.g., entangled, embedded, incorporated, encapsulated, bound to the surface, or otherwise associated with the nanoparticle). Preferably such a bioactive agent is associated to a nanoparticle through a compound of the invention acting as a linker between bioactive agent and nanoparticle. These aspects of the present compounds and compositions thereof are part of an international application filed concurrently, which is incorporated herein in its entirety.

Nanoparticles may also be grouped together (optionally with a dispersing agent) to form a nanocluster. The independent formulation of each nanoparticle type before cluster formation and a special arrangement of nanoparticles within the cluster can allow controlling the duration and concentration of a bioactive ingredient.

In one embodiment of the present invention, one or more non-derivatized or derivatized compounds of the invention may be incorporated into, attached to or adsorbed to a nanoparticle. Preferably, lipid coated nanoparticles (LCN) may be formed from nanosized core particles and one or more compounds of the present invention and optionally one or more co-lipids. In any given lipid coated nanoparticle, the lipids may be in the form of a monolayer or a bilayer. In the case of more than one mono- or bilayer, the mono- or bilayers are generally concentric. Coating of the nanoparticles is preferably carried out in a solution comprising the compounds of the invention and by allowing sufficient time to allow the compounds to coat the nanoparticles (using techniques known in the art, see e.g. Journal of Controlled Release, Vol 137(1), 69-77, 2009). In any given lipid coated nanoparticle, the lipids may be in the form of a monolayer or a bilayer. In the case of more than one mono- or bilayer, the mono- or bilayers are generally concentric.

Various methods can be employed to fabricate nanoparticles of suitable size. These methods include vaporization methods (e.g., free jet expansion, laser vaporization, spark erosion, electro explosion and chemical vapor deposition), physical methods involving mechanical attrition (e.g., the pearlmilling technology, Elan Nanosystems, Ireland), and interfacial deposition following solvent displacement.

As those skilled in the art will recognize, any of the present compounds and vesicular compositions containing the compounds of the invention, with or without bioactive agents, may be lyophilized for storage, and reconstituted in, for example, an aqueous medium (such as sterile water or phosphate buffered solution, or aqueous saline solution), preferably under vigorous agitation. If necessary, additives may be included to prevent agglutination or fusion of the lipids as a result of lyophilisation. Useful additives include, without limitation, sorbitol, mannitol, sodium chloride, glucose, trehalose, polyvinylpyrrolidone and poly(ethylene glycol), for example, PEG 400.

As indicated above, the present compounds and in particular the liposomal compositions of the present invention are particularly suitable for use as carriers for a targeted delivery of bioactive agents or for use as antigen display systems. Thus, the compounds of the present invention are particularly applicable for use in vitro and/or in vivo in methods for the treatment of diseases, for which a targeted delivery of one or more specific biologically active agents is desirable or required, as well as for use in methods in vitro/in vivo diagnostic applications. These aspects of the present compounds and compositions thereof are part of an international application filed concurrently, which is incorporated herein in its entirety.

In a further aspect, the present invention relates to a kit comprised of a container that is compartmentalized for holding the various elements of the kit. One compartment may contain a predetermined quantity of either a compound of the present invention or a vesicular composition thereof. In case of vesicular compositions, these may be with or without a pH buffer to adjust the composition pH to physiological range of about 7 to about 8, or else in lyophilized or freeze dried form for reconstitution at the time of use. Also included within the kit will be other reagents and instructions for use.

The present invention is further described in the following examples.

EXAMPLES

Materials:

Cholesterol and POPC are purchased from Avanti Polar Lipids (Alabaster, Ala.). All Protected amino acids are obtained from Novabiochem. Diphenyldiazomethane resin D-2230 is obtained from Bachem AG. All other chemicals and solvents are A.R. grade or above.

2,3-Bis(tetradecyloxy)propan-1-amine is synthesized according to Kokotos et al. Chemistry-A European Journal, 2000, vol. 6, #22, 4211-4217. In an analogous way bis(3-((Z)-octadec-9-enyloxy)propyl)amine is obtained from oleyl methanesulfonate and bis(3-hydroxypropyl)amine (see MaGee et al., J. Journal of Organic Chemistry, 2000, vol. 65, #24, 8367-8371).

Example 1: Synthesis of (2S)-2-(((9H-fluoren-9-yl)methoxy)carbonylamino)-glutamic acid-α-tert-butylester-γ-2,3-bis(tetradecyloxy)propyl-amide

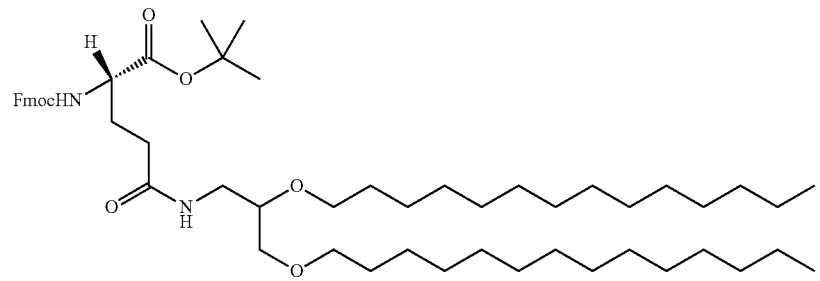

15 g of Fmoc-Glu(OSu)OtBu ((2S)—N_□-(9-fluorenylmethyloxycarbonyl)-glutamic acid α-tert-butyl-ester γ-N-hydroxysuccinimide ester) are dissolved in dichloromethane at room temperature. After addition of 15.3 g of 2,3-bis(tetradecyloxy)propan-1-amine, the mixture is stirred for 17 hours and evaporated to dryness. The residue is dissolved in a minimum amount of dichloromethane and purified by column chromatography using $SiO_2$ as solid phase and methyl tert. butylether/hexane/7:3 as eluent. After evaporation of product fractions 25.5 g of (2S)-2-(((9H-fluoren-9-yl)methoxy)carbonylamino)-glutamic acid-α-tert-butylester-γ-2,3-bis(tetradecyloxy)propyl-amide are obtained as a colorless solid. $^1$H-NMR in $CDCl_3$ (TMS as internal standard), chemical shift in ppm: 7.76 (d, 2H, Fmoc), 7.61 (d, 2H, Fmoc), 7.25-7.43 (m, 4H, Fmoc), 6.13 (bs, NH, 1H), 5.60 (bs, NH, 1H), 4.39, 4.18-4.25 (d and m, 4H), 3.21-3.62 (m, 9H), 1.97-2.23 (m, 4H), 1.51-1.60 (m, 4H), 1.47 (s, 9H), 1.25 (m, 44H, $CH_2$), 0.84-0.91 (m, 6H, 2× alkyl-$CH_3$).

Example 2: Synthesis of (2S)-2-(((9H-fluoren-9-yl)methoxy)carbonylamino)-glutamic acid-γ-2,3-bis(tetradecyloxy)propyl-amide

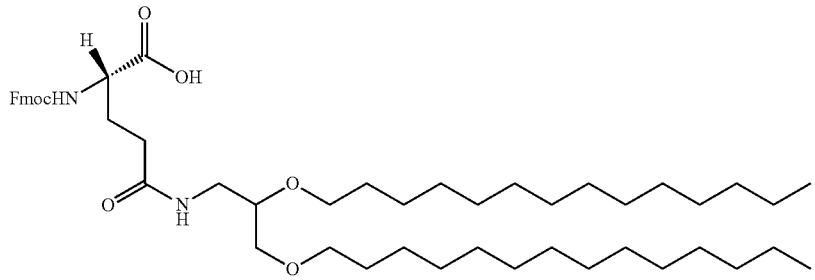

4.6 g (5.1 mmol) of (2S)-2-(((9H-fluoren-9-yl)methoxy)carbonylamino)-glutamic acid-α-tert-butylester-γ-2,3-bis(tetradecyloxy)propyl-amide are dissolved in 25 ml dichloromethane in a 100 ml flask and treated with 25 ml trifluoroacetic acid. After 1 h the ester group is completely cleaved and the solution is poured onto 50 ml of cold water. The organic layer is extracted, washed to neutral pH with water and dried over Na2SO4. The organic layer is filtered off and the solvent evaporated to afford 4.2 g of the desired product (5.0 mmol, 98% yield, TLC: MtBE/hexane 7:3; Rf=0.43.

Example 3: Synthesis of (2S)-glutamic acid-γ-(2,3-bis(tetradecyloxy)propyl)amide

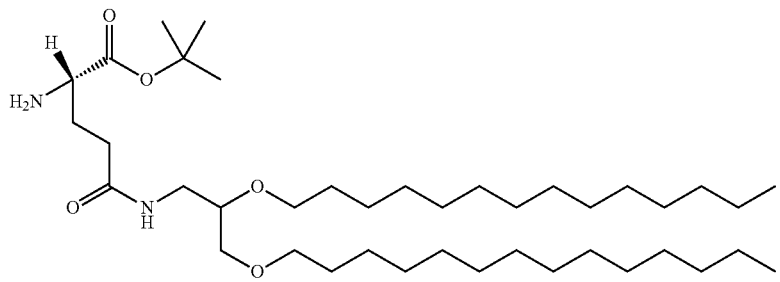 [SMILES: CCCCCCCCCCCCCCOCC(CNC(=O)CC[C@H](N)C(=O)OC(C)(C)C)OCCCCCCCCCCCCCC]

5 g of (2S)-2-(((9H-fluoren-9-yl)methoxy)carbonylamino)-glutamic acid-α-tert-butylester-γ-2,3-bis(tetradecyloxy)propyl-amide are added to 85 ml of N,N-dimethylformamide. 2.6 ml of piperidine are added to the mixture. The mixture is stirred for three hours at room temperature and then evaporated to dryness under vacuum to give 5.2 g of (2S)-glutamic acid-γ-(2,3-bis(tetradecyloxy)propyl) amide as a colorless solid, which can be used in the preparation of lipidic vesicles or for prior derivatization with an active agent or a spacer group.

Example 4: Synthesis of (R)-2-amino-N1-(2-(4-methoxybenzamido)ethyl)-N4,N4-bis(3-((Z)-octadec-9-enyloxy)propyl)succinamide

(a) Synthesis of N-(2-aminoethyl)-4-methoxybenzamide

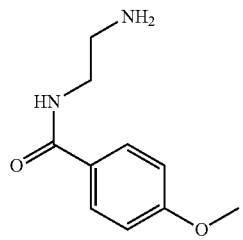

3.0 g 4-Methoxybenzoyl chloride are added to 30 mL 1,2-diaminoethane in dichloromethane at −78° C. and subsequently allowed to warm to 23° C. An aqueous acid-base workup and evaporation to dryness under vacuum give 1.65 g of N-(2-aminoethyl)-4-methoxybenzamide, a pale yellow oil. $^1$H-NMR in CDCl$_3$ (TMS as internal standard), chemical shift in ppm: 8.53 (t, 1H, NH), 7.91 (d, 2H, Benz), 6.99 (d, 2H, Benz), 4.75 (bs, 2H, NH$_2$), 3.81 (s, 3H, CH$_3$), 3.39, (dd, 2H, CH$_2$), 2.82 (t, 2H, CH$_2$).

(b) Synthesis of (R)-tert-butyl 3-(((9H-fluoren-9-yl)methoxy)carbonylamino)-4-(2-(4-methoxybenzamido)ethylamino)-4-oxobutanoate

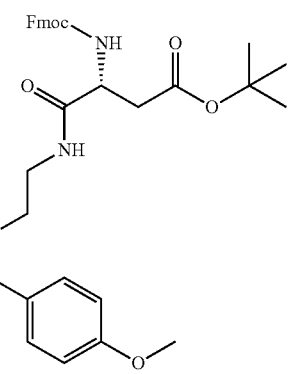

3.0 g 2 N-(2-aminoethyl)-4-methoxybenzamide (obtained in step (a)) and 1.70 mL N-methylmorpholine in DMF (0° C.) are added to a solution of 6.35 g Fmoc-Asp(OtBu)-OH, 1.70 mL N-methylmorpholine and 2.00 mL isobutylchloroformate in ethylacetate (−12° C.) and stirred for 3 h while allowing to warm to 23° C. Dilution of the resulting suspension with ethylacetate, followed by an aqueous acid-base workup and evaporation to dryness under vacuum yielded 9.55 g (R)-tert-butyl 3-(((9H-fluoren-9-yl)methoxy)carbonylamino)-4-(2-(4-methoxybenzamido)ethylamino)-4-oxobutanoate. This crude material is suspended in isopropylether for 23 h, then filtered off and dried to furnish 4.47 g (R)-tert-butyl 3-(((9H-fluoren-9-yl)methoxy)carbonylamino)-4-(2-(4-methoxybenzamido)ethylamino)-4-oxobutanoate as white crystals. $^1$H-NMR in $CDCl_3$ (TMS as internal standard), chemical shift in ppm: 8.28 (t, 1H, NH), 8.07 (t, 1H, NH), 7.89 (d, 2H, Fmoc), 7.81 (d, 2H, Benz), 7.71-7.60 (m, 2H, Fmoc and 1H, NH), 7.46-7.27 (m, 4H, Fmoc), 6.96 (d, 2H, Benz), 4.35-4.20 (m, 3H, Fmoc, and 1H CH), 3.78 (s, 3H, $CH_3$), 3.40-3.20, (m, 4H, 2×$CH_2$), 2.69 (dd, 1H, $CH_2$), 2.46 (dd, 1H, $CH_2$), 1.37 (s, 9H, 3×$CH_3$).

(c) Synthesis of (R)-3-(((9H-fluoren-9-yl)methoxy)carbonylamino)-4-(2-(4-methoxybenzamido)ethylamino)-4-oxobutanoic sodium acetate

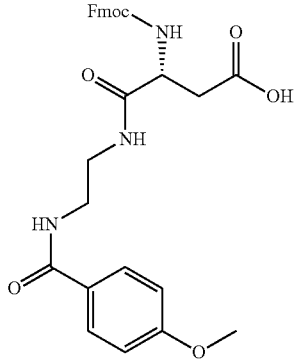

30.0 mL of trifluoroacetic acid are added to 3.0 g of (R)-tert-butyl 3-(((9H-fluoren-9-yl)methoxy)carbonylamino)-4-(2-(4-methoxybenzamido)ethylamino)-4-oxobutanoate (obtained in step (b)) in dichloromethane at 23° C. Upon completion of the reaction aq. $NaHCO_3$ is added to furnish a white precipitate which is washed dichloromethane and dried to yield 2.55 g (R)-3-(((9H-fluoren-9-yl)methoxy)carbonylamino)-4-(2-(4-methoxybenzamido) ethylamino)-4-oxobutanoic sodium acetate as a white powder. $^1$H-NMR in $SO(CD_3)/CD_3OD$, 1:1, (TMS as internal standard), chemical shift in ppm: 7.85-7.79 (m, 2H, Fmoc and 2H, Benz), 7.68 (d, 2H, Fmoc), 7.45-7.29 (m, 4H, Fmoc), 6.93 (d, 2H, Benz), 4.51-4.17 (m, 3H, Fmoc and 1H, CH), 3.78 (s, 3H, $CH_3$), 3.47-3.34, (m, 4H, 2×$CH_2$), 2.82 (dd, 1H, $CH_2$), 2.63 (dd, 1H, $CH_2$).

(d) Synthesis of (9H-fluoren-9-yl)methyl (R,Z)-1-(4-methoxyphenyl)-10-(3-((Z)-octadec-9-enyloxy)propyl)-1,6,9-trioxo-14-oxa-2,5,10-triazadotriacont-23-en-7-yl carbamate

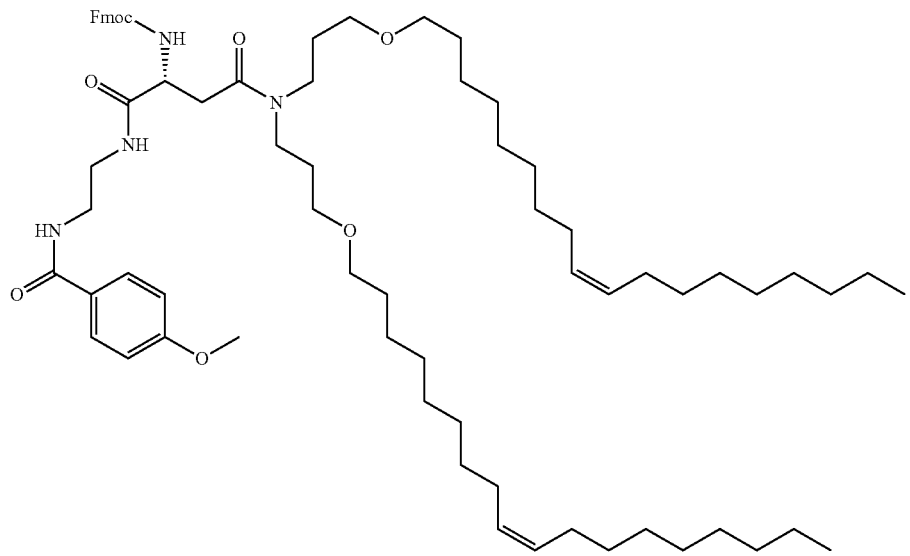

0.48 g of (R)-3-(((9H-fluoren-9-yl)methoxy)carbonylamino)-4-(2-(4-methoxybenzamido)ethylamino)-4-oxobutanoic sodium acetate (obtained in step (c)) in dimethylformamide are cooled to 10° C. and then 0.46 g bis(3-((Z)-octadec-9-enyloxy)propyl)amine, 0.37 g COMU and 0.20 g DIPEA are added subsequently. After stirring at 23° C. for 20 h the solution is filtered through a pad of Alox and this rinsed with little dimethylformamide. The filtrate is diluted with ethylacetate, washed with water and evaporation to dryness under vacuum give 1.12 g orange oil which is purified by column chromatography to yield 0.41 g (9H-fluoren-9-yl)methyl (R,Z)-1-(4-methoxyphenyl)-10-(3-((Z)-octadec-9-enyloxy)propyl)-1,6,9-trioxo-14-oxa-2,5,10-triazadotriacont-23-en-7-yl-carbamate. $^1$H-NMR in $CDCl_3$ (TMS as internal standard), chemical shift in ppm: 7.86 (d, 2H, Benz), 7.69 (d, 2H, Fmoc), 7.55 (d, 2H, Fmoc), 7.42-7.23 (m, 4H, Fmoc and 1H, NH), 6.88 (d, 2H, Benz and 1H, NH), 6.12 (bd, 1H, NH), 5.41-5.26 (m, 4H, 4×CH), 4.60-4.33 (m, 3H, Fmoc), 4.17 (t, 1H, CH), 3.82 (s, 3H, $CH_3$), 3.62-3.23, (m, 16H, 8×$CH_2$ and 1H, $CH_2$), 2.73 (dd, 1H, $CH_2$), 2.05-1.95 (m, 8H, 4×$CH_2$), 1.85-1.65 (m, 4H, 2×$CH_2$), 1.57-1.45 (m, 4H, 2×$CH_2$), 1.24 (bs, 44H, 22×$CH_2$), 0.88 (t, 6H, 2×$CH_3$).

(e) Synthesis of (R)-2-amino-N1-(2-(4-methoxyben-zamido)ethyl)-N4,N4-bis(3-((Z)-octadec-9-enyloxy)propyl)succinamide

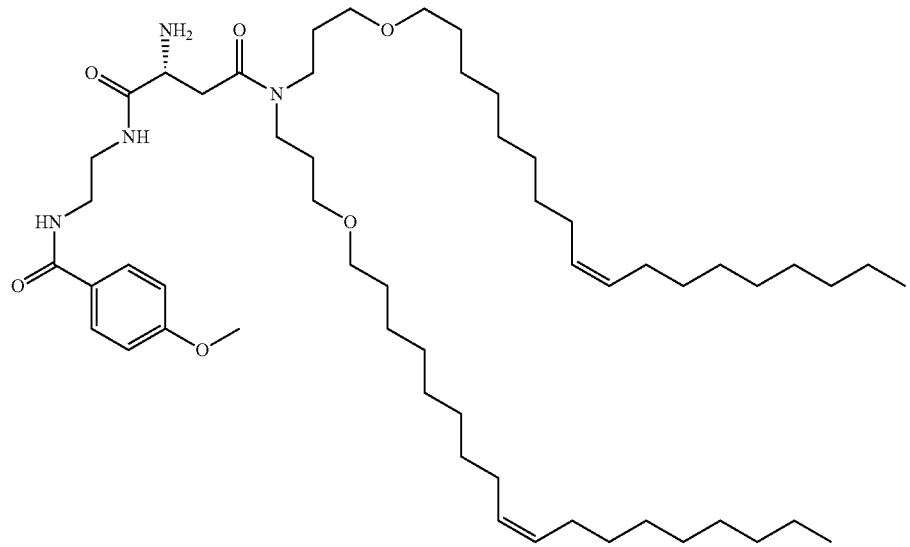 [SMILES: CCCCCCCC/C=C\CCCCCCCCOCCCN(CCCOCCCCCCCC/C=C\CCCCCCCC)C(=O)C[C@@H](N)C(=O)NCCNC(=O)c1ccc(OC)cc1]

0.75 g of diethylamine is added to 2.12 g of (9H-fluoren-9-yl)methyl (R,Z)-1-(4-methoxyphenyl)-10-(3-((Z)-octadec-9-enyloxy)propyl)-1,6,9-trioxo-14-oxa-2,5,10-triazadotriacont-23-en-7-yl-carbamate (obtained in step (d)) in dichloroethane, stirred for 26 h followed by evaporation to dryness under vacuum to give 1.90 g crude material which is purified by adsorption to 20 g Dowex Monosphere and subsequent desorption by ammonia in ethanol to yield 1.09 g (R)-2-amino-N1-(2-(4-methoxybenzamido)ethyl)-N4,N4-bis(3-((Z)-octadec-9-enyloxy)propyl)succinamide.
$^1$H-NMR in CDCl$_3$ (TMS as internal standard), chemical shift in ppm: 7.88 (d, 2H, Benz and 1H, NH), 7.64 (t, 1H, NH), 6.89 (d, 2H, Benz), 5.42-5.26 (m, 4H, 4×CH), 3.82 (s, 3H, CH$_3$), 3.65-3.49, (m, 4H, 2×CH$_2$), 3.42-3.28 (m, 12H, 6×CH$_2$ and 1H, CH), 2.99 (dd, 1H, CH$_2$), 2.71 (dd, 1H, CH$_2$), 2.10-1.92 (m, 8H, 4×CH$_2$ and 2H, NH$_2$), 1.85-1.67 (m, 4H, 2×CH$_2$), 1.60-1.47 (m, 4H, 2×CH$_2$), 1.28 (bs, 44H, 22×CH$_2$), 0.90 (t, 6H, 2×CH$_3$). MS: 947.9 [M+Na]$^+$.

Example 5: Synthesis of (41S)-1-amino-41-(3-((2,3-bis(tetradecyloxy)propyl)amino)-3-oxopropyl)-39-oxo-3,6,9,12,15,18,21,24,27,30,33,36-dodecaoxa-40-azatetracontan-42-oic acid (a) Synthesis of Fmoc-Glu(DMA)-OtBu Resin 3.85 g of diphenyldiazomethane resin (3.3 mmol) are washed twice with 30 ml DCM in a 100 ml SPPS reactor and treated with a solution of 4.2 g of (2S)-2-(((9H-fluoren-9-yl)methoxy)carbonylamino)-glutamic acid-γ-2,3-bis(tetradecyloxy)propyl-amide (see example 2, 1.5 eq., 5.0 mmol) in 30 ml DCM over night. The solution is filtered off and the resin is washed with DCM four times. To destroy eventually un-reacted diphenyldiazomethane the resin is treated with 125 μl acetic acid (0.5 eq., 2.2 mmol) in 30 ml DCM for 15 minutes and washed afterwards three times alternating with 30 ml dimethylformamide and isopropanol. The resin is washed twice with diisopropyl ether and dried over night in vacuo. 6.7 g of the desired product are obtained (>100% of theory, yield in theory 6.5 g). The loading of the resin is determined to 0.49 mmol/g by UV measurement of the Fmoc cleavage product at 304 nm (maximum loading in theory 0.51 mmol/g).

(b) Synthesis of H-Glu-OtBu-NH-PEG11-Glu(DMA)-diphenylmethyl resin

H-Glu-OtBu-NH-PEG11-Glu(DMA)-diphenylmethyl resin is obtained through conventional solid phase synthesis by the following reaction sequence:

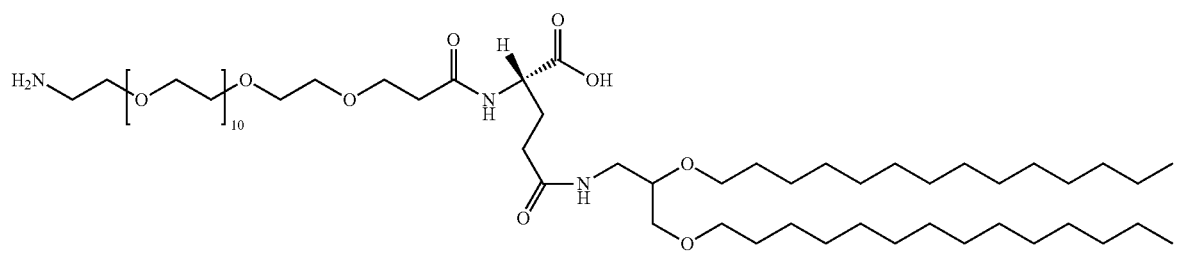

1) cleavage of the Fmoc group of the Fmoc-Glu(DMA)-OtBu resin with piperidin in DMF,
(2) condensation with Fmoc-NH-PEG11-COOH using HTBU in DMF and DIPEA,
(3) cleavage of the Fmoc group of the Fmoc-NH-PEG11-Glu(DMA)-OtBu resin with piperidin in DMF, (c) Cleavage and Deprotection of H-Glu-OtBu-NH-PEG11-Glu(DMA)-diphenylmethyl resin The desired compound can be obtained by cleavage from the resin e.g. by treatment with trifluoroacetic acid and triisopropylsilane.

Example 6: Preparation of Anis Amide Decorated Liposomes 470 mg POPC, 60 mg Chol and 13.5 mg anis amide lipid (see example 4) are dissolved in 750 μL ethanol (96%) at 55° C. and injected into 4.25 mL of PBS pH 7.4. Molar ratio of the used lipids is 77.99:18.83:1.02:0.27. After extrusion through 100 nm polycarbonate membrane the liposomes have an average size of 110 nm with a PDI of 0.068. According to HPLC analysis the anis amide lipid content is 72% of the theoretical value.

Example 7: Synthesis of NH$_2$-PEG$_8$-PA-Glu(DMA)-amide

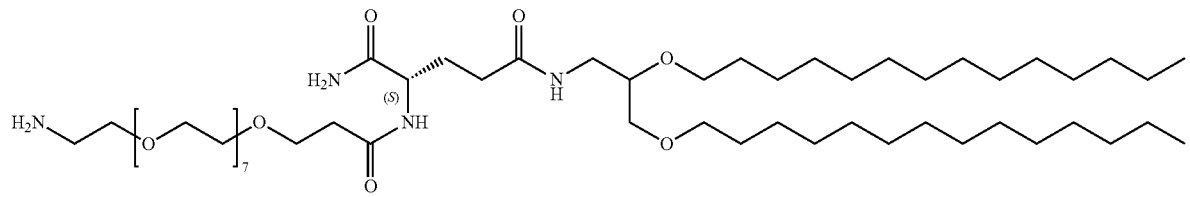

(a) Synthesis of Fmoc-Glu(DMA)-Sieber Resin: (See Example 16)

(b) Synthesis of NH$_2$-PEG$_8$-PA-Glu(DMA)-Sieber Resin

NH$_2$-PEG$_8$-PA-Glu(DMA)-Sieber resin is obtained through conventional solid phase synthesis by the following reaction sequence:
(1) cleavage of the Fmoc group of the Fmoc-Glu(DMA)-Sieber resin with piperidin in DMF,
(2) condensation with Fmoc-NH-PEG$_8$-PA using HBTU in DMF and DIPEA and finally
(3) cleavage of the Fmoc group of the Fmoc-NH-PEG$_8$-PA-Glu(DMA)-Sieber resin with piperidin in DMF.

(c) Synthesis of NH$_2$-PEG$_8$-PA-Glu(DMA)-amide

The product is cleaved from the NH$_2$-PEG$_8$-PA-Glu(DMA)-Sieber resin using trifluoroacetic acid in dichloromethane. ESI-MS: monoisotopic M$_W$ $_{calc.}$=1034.8, M$_W$ [M+H]$^+$=1035.9.

The invention claimed is:
1. A compound of formula I

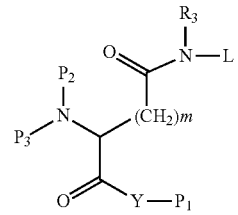

wherein
Y represents O, N, S or a covalent bond,
P$_1$ represents H, an Y-protecting group or an Y-activating group or a spacer group,
P$_2$ and P$_3$ represent independently of each other H, an amino-protecting group or a spacer group, or P$_2$ and P$_3$ form together with the N to which they are bound a ring structure,
L is a group of formula (a)

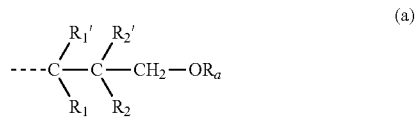

wherein the dashed line represents the linkage to N,
R$_1$, represents H or a group of formula —(CH$_2$)$_2$—OR$_{b1}$,
R$_{1'}$ represents H or a group of formula —(CH$_2$)$_2$—OR$_{b2}$,
R$_2$ represents H or a group of formula —CH$_2$—OR$_c$,
R$_{2'}$ represents H or a group of formula —OR$_d$ or —CH$_2$—OR$_d$,
R$_3$ represents H or a group of formula —(CH$_2$)$_2$—OR$_e$ or —(CH$_2$)$_3$—OR$_e$,
R$_a$, R$_{b1}$, R$_{b2}$, R$_c$, R$_d$ and R$_e$ represent independently of each other a saturated or unsaturated, straight or branched hydrocarbon chain, and
m is 1, 2 or 3,
with the proviso that at least one of R$_1$, R$_{1'}$, R$_2$, R$_{2'}$, R$_3$ is not H.
2. Compound according to claim 1, wherein R$_3$ is H, and L is a group of formula (b) or (c)

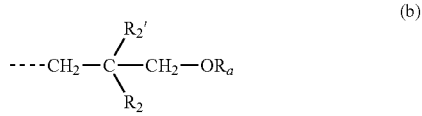

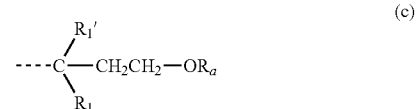

wherein the dashed line represents the linkage to N, and P$_1$, P$_2$, P$_3$, Y, R$_1$, R$_{1'}$, R$_2$, R$_{2'}$, R$_a$, and m are defined as in claim 1, with the proviso that in formula (b) at least one of $R_2$ and $R_{2'}$ is not H, and in formula (c) at least one of $R_1$ and $R_{1'}$ is not H.

3. A compound according to claim 2, wherein L is a group of formula (b1), (b2), (b3) or (b4):

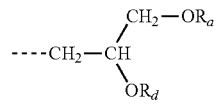

(b1)

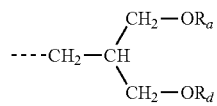

(b2)

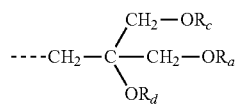

(b3)

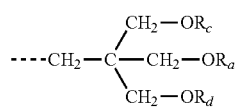

(b4)

wherein the dashed line represents the linkage to N, and wherein $R_a$, $R_c$ and $R_d$ are independently of each other a saturated or unsaturated, straight or branched hydrocarbon chain.

4. A compound according to claim 2, wherein L is a group of formula (c1) or (c2):

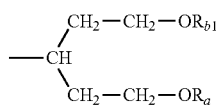

(c1)

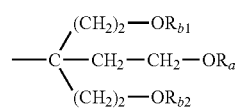

(c2)

wherein the dashed line represents the linkage to N, and wherein $R_a$, $R_{b1}$, $R_{b2}$ are independently of each other a saturated or unsaturated, straight or branched hydrocarbon chain.

5. A compound according to claim 1 wherein
$R_1$, $R_{1'}$, $R_2$ and $R_{2'}$ are H,
$R_3$ is a group of formula —$(CH_2)_2$—$OR_e$ or —$(CH_2)_3$—$OR_e$, and
$P_1$, $P_2$, $P_3$, Y, $R_a$, $R_e$ and m are defined as in claim 1.

6. A compound according to claim 1 having formula II or III

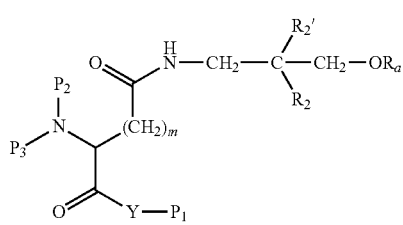

II

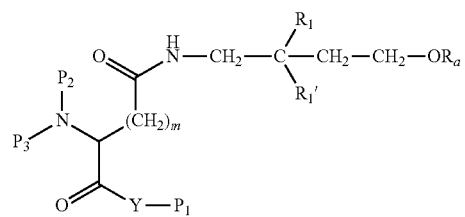

III wherein

Y represents O, N, S or a covalent linkage, $P_1$ represents H, an Y-protecting group or an Y-activating group or a spacer group, $P_2$ and $P_3$ represent independently of each other H, an amino-protecting group or a spacer group, or $P_2$ and $P_3$ form together with the N to which they are bound a ring structure, $R_1$ represents H or a group of formula —$(CH_2)_2$—$OR_{b1}$, $R_{1'}$ represents H or a group of formula —$(CH_2)_2$—$OR_{b2}$, $R_2$ represents H or a group of formula —$CH_2$—$OR_c$, $R_{2'}$ represents H or a group of formula —$OR_d$ or —$CH_2$—$OR_d$, $R_a$, $R_{b1}$, $R_{b2}$, $R_c$ and $R_d$ represent independently of each other a saturated or unsaturated, straight or branched hydrocarbon chain, and m is 1, 2 or 3, with the proviso that in formula II at least one of $R_2$ and $R_{2'}$ is not H, and in formula III at least one of $R_1$ and $R_{1'}$ is not H.

7. A compound according to claim 6 having formula IIa, IIb, IIc or IId,

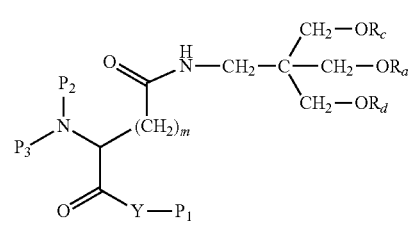

IIa

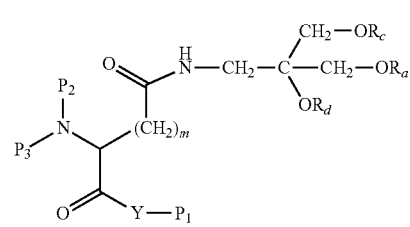

IIb

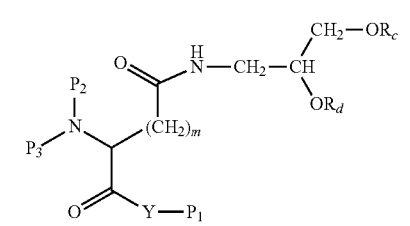

IIc

-continued

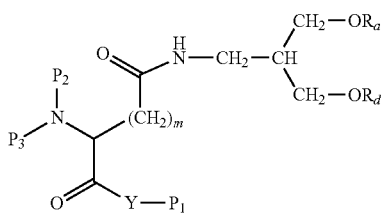

IId wherein

Y represents O, N, S or a covalent linkage, $P_1$ represents H, an Y-protecting group or an Y-activating group or a spacer group, $P_2$ and $P_3$ represent independently of each other H, an amino-protecting group or a spacer group, or $P_2$ and $P_3$ form together with the N to which they are bound a ring structure, $R_a$, $R_c$ and $R_d$ represent independently of each other a saturated or unsaturated, straight or branched hydrocarbon chain, and m is 1, 2 or 3.

8. A compound according to claim 6 having formula IIIa or IIIb,

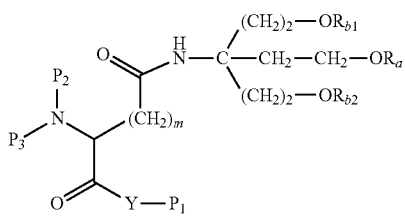

IIIa

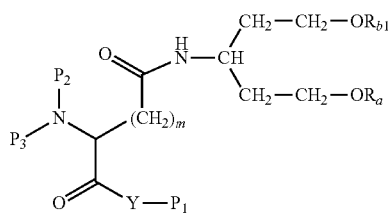

IIIb wherein

Y represents O, N, S or a covalent linkage, $P_1$ represents H, a Y-protecting group or a Y-activating group or a spacer group, $P_2$ and $P_3$ represent independently of each other H, an amino-protecting group or a spacer group, or $P_2$ and $P_3$ form together with the N to which they are bound a ring structure, $R_a$, $R_{b1}$ and $R_{b2}$ represent independently of each other a saturated or unsaturated, straight or branched hydrocarbon chain, and m is 1, 2 or 3.

9. A compound according to claim 1 having formula IVa or IVb,

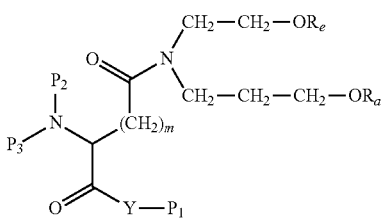

IVa

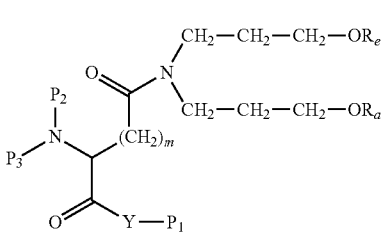

IVb wherein

Y represents O, N, S or a covalent linkage, $P_1$ represents H, an Y-protecting group or an Y-activating group or a spacer group, $P_2$ and $P_3$ represent independently of each other H, an amino-protecting group or a spacer group, or $P_2$ and $P_3$ form together with the N to which they are bound a ring structure, $R_a$ and $R_e$ represent independently of each other a saturated or unsaturated, straight or branched hydrocarbon chain, and m is 1, 2 or 3.

10. Compound according to claim 1, wherein $R_a$, $R_{b1}$, $R_{b2}$, $R_c$, $R_d$ and $R_e$ are independently of each other straight or branched C(10-22)alkyl, C(10-22)alkenyl or C(10-22)alkynyl.

11. Compound according to claim 10, wherein C(10-22)alkenyl and C(10-22)alkynyl have 1, 2, 3 or 4 unsaturated bonds.

12. Compound according to claim 1, wherein at least one of $P_1$, $P_2$ and $P_3$ is a spacer group.

13. Compound according to claim 12, wherein the spacer group is chosen from an alkylene chain optionally further comprising one or more groups selected from ketone, ester, ether, amino, amide, amidine, carbamate, thiocarbamate, glycerol, urea, thiourea, double bonds or aromatic rings.

14. A compound according to claim 13 wherein the spacer group is polyethylene glycol or an end-capped polyethylene glycol.

15. A drug delivery system or as an antigen display system comprising a compound according to claim 1.

16. Vesicular composition comprising at least one compound of formula I according to claim 1, optionally in admixture with one or more other vesicle-forming compounds.

17. Vesicular composition according to claim 16, wherein the vesicular composition comprises a liposome, a micelle or a nanoparticle.

18. A kit comprising a compound according to claim 1.

19. A kit comprising a vesicular composition according to claim 16.

20. Compound according to claim 10, wherein C(10-22)alkenyl and C(10-22)alkynyl have 1 or 2 unsaturated bonds.

* * * * *